(12) United States Patent
Schaeffer

(10) Patent No.: US 9,314,593 B2
(45) Date of Patent: Apr. 19, 2016

(54) MEDICAL DEVICES FOR THE IDENTIFICATION AND TREATMENT OF BODILY PASSAGES

(71) Applicant: Cook Medical Technologies LLC, Bloomington, IN (US)

(72) Inventor: Darin Schaeffer, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 185 days.

(21) Appl. No.: 14/033,644

(22) Filed: Sep. 23, 2013

(65) Prior Publication Data

US 2014/0088355 A1 Mar. 27, 2014

Related U.S. Application Data

(60) Provisional application No. 61/704,652, filed on Sep. 24, 2012.

(51) Int. Cl.
| | |
|---|---|
| A61B 1/00 | (2006.01) |
| A61M 25/01 | (2006.01) |
| A61B 17/24 | (2006.01) |
| A61B 17/34 | (2006.01) |
| A61B 1/04 | (2006.01) |
| A61B 1/06 | (2006.01) |

(Continued)

(52) U.S. Cl.
CPC .......... *A61M 25/0113* (2013.01); *A61B 1/0052* (2013.01); *A61B 1/04* (2013.01); *A61B 1/06* (2013.01); *A61B 17/24* (2013.01); *A61B 17/29* (2013.01); *A61B 17/3421* (2013.01); *A61M 1/0023* (2013.01); *A61M 25/0136* (2013.01); *A61M 25/0147* (2013.01); *A61B 1/0057* (2013.01); *A61B 1/233* (2013.01); *A61B 2017/003* (2013.01); *A61B 2017/00323* (2013.01); *A61B 2017/22074* (2013.01); *A61B 2017/345* (2013.01); *A61B 2017/3445* (2013.01); *A61M 25/0052* (2013.01); *A61M 25/0144* (2013.01); *A61M 2025/1013* (2013.01)

(58) Field of Classification Search
USPC ........... 600/106, 107, 114, 144, 146; 604/528
See application file for complete search history.

(56) References Cited

U.S. PATENT DOCUMENTS

| | | |
|---|---|---|
| 3,521,620 A | 7/1970 | Cook |
| 3,625,200 A | 12/1971 | Muller |

(Continued)

FOREIGN PATENT DOCUMENTS

| | | |
|---|---|---|
| EP | 2368481 | 9/2011 |
| GB | 2465621 | 6/2010 |

(Continued)

OTHER PUBLICATIONS

European Patent Office, Extended European Search Report, App. No. 1318580.2, Jan. 7, 2014, pp. 1-5.

(Continued)

*Primary Examiner* — Matthew J Kasztejna
(74) *Attorney, Agent, or Firm* — Buchanan Nipper

(57) ABSTRACT

Medical devices are described. More particularly, medical devices and methods for the identification and treatment of bodily passages, such as sinus cavities, are described herein. An exemplary medical device comprises an elongate member, a handle, and a wire member. The elongate member is moveable between a first straight, or substantially straight, configuration to a second curved configuration.

20 Claims, 12 Drawing Sheets

(51) Int. Cl.
*A61B 17/29* (2006.01)
*A61M 1/00* (2006.01)
*A61B 1/005* (2006.01)
A61B 1/233 (2006.01)
A61B 17/00 (2006.01)
A61B 17/22 (2006.01)
A61M 25/10 (2013.01)
A61M 25/00 (2006.01)

(56) References Cited

U.S. PATENT DOCUMENTS

| | | | |
|---|---|---|---|
| 4,726,374 A | 2/1988 | Bales et al. | |
| 4,826,087 A | 5/1989 | Chinery | |
| 5,168,864 A * | 12/1992 | Shockey | 600/144 |
| 5,308,318 A | 5/1994 | Plassche, Jr. | |
| 5,380,305 A | 1/1995 | Ghouri | |
| 5,447,503 A | 9/1995 | Miller | |
| 5,460,616 A | 10/1995 | Weinstein et al. | |
| 5,477,860 A | 12/1995 | Essen-Moller | |
| 5,489,278 A | 2/1996 | Abrahamson | |
| 5,522,400 A | 6/1996 | Williams | |
| 5,674,197 A | 10/1997 | van Muiden et al. | |
| 5,685,858 A | 11/1997 | Kawand | |
| 5,738,664 A | 4/1998 | Erskine et al. | |
| 5,908,403 A | 6/1999 | Bosma et al. | |
| 5,954,050 A | 9/1999 | Christopher | |
| 5,989,241 A | 11/1999 | Plishka et al. | |
| 6,033,378 A | 3/2000 | Lundquist et al. | |
| 6,159,158 A | 12/2000 | Lowe | |
| 6,159,177 A | 12/2000 | Amos, Jr. et al. | |
| 6,500,167 B1 | 12/2002 | Webster, Jr. | |
| 6,527,737 B2 | 3/2003 | Kaneshige | |
| 6,530,913 B1 | 3/2003 | Giba et al. | |
| 6,673,060 B1 | 1/2004 | Fleming, III | |
| 7,037,290 B2 | 5/2006 | Gardeski et al. | |
| 7,232,462 B2 | 6/2007 | Schaeffer | |
| 7,269,453 B2 | 9/2007 | Mogul | |
| 7,520,876 B2 | 4/2009 | Ressemann et al. | |
| 7,641,630 B2 | 1/2010 | Accisano, III et al. | |
| 7,658,305 B2 | 2/2010 | Voegele et al. | |
| 7,678,099 B2 | 3/2010 | Ressemann et al. | |
| 7,736,331 B2 | 6/2010 | Accisano, III et al. | |
| 7,740,608 B2 | 6/2010 | Lampropoulos et al. | |
| 7,785,252 B2 | 8/2010 | Danitz et al. | |
| 7,785,315 B1 | 8/2010 | Muni et al. | |
| 7,803,130 B2 | 9/2010 | Ryan et al. | |
| 7,811,277 B2 | 10/2010 | Boulais | |
| 7,867,218 B1 | 1/2011 | Voda | |
| 7,892,233 B2 | 2/2011 | Hall et al. | |
| 7,909,814 B2 | 3/2011 | Accisano, III et al. | |
| 7,959,601 B2 | 6/2011 | McDaniel et al. | |
| 7,959,644 B2 | 6/2011 | Shriver | |
| 8,029,461 B2 | 10/2011 | Thielen et al. | |
| 8,066,664 B2 | 11/2011 | LaDuca et al. | |
| 8,070,693 B2 | 12/2011 | Ayala et al. | |
| 8,083,879 B2 | 12/2011 | Swinehart et al. | |
| 8,216,210 B2 | 7/2012 | Ostrovsky et al. | |
| 8,425,466 B2 | 4/2013 | Sargent, Jr. | |
| 8,496,645 B2 | 7/2013 | Eells et al. | |
| 8,535,310 B2 | 9/2013 | Hardin, Jr. et al. | |
| 8,535,349 B2 | 9/2013 | Chen et al. | |
| 8,579,802 B2 * | 11/2013 | Robertson | 600/144 |
| 8,657,805 B2 | 2/2014 | Peh et al. | |
| 8,702,559 B2 * | 4/2014 | Jeong | 477/3 |
| 8,734,426 B2 | 5/2014 | Ahmed et al. | |
| 8,740,843 B2 | 6/2014 | Eaton et al. | |
| 8,758,231 B2 | 6/2014 | Bunch et al. | |
| 2002/0115983 A1 | 8/2002 | Sekino et al. | |
| 2003/0004460 A1 | 1/2003 | Bedell | |
| 2005/0256452 A1 | 11/2005 | DeMarchi et al. | |
| 2006/0063973 A1 | 3/2006 | Makower et al. | |
| 2006/0178562 A1 * | 8/2006 | Saadat et al. | 600/142 |
| 2007/0167682 A1 | 7/2007 | Goldfarb et al. | |
| 2007/0203474 A1 * | 8/2007 | Ryan et al. | 604/528 |
| 2007/0250105 A1 | 10/2007 | Ressemann et al. | |
| 2007/0293727 A1 | 12/2007 | Goldfarb | |
| 2008/0097154 A1 | 4/2008 | Makower et al. | |
| 2008/0125756 A1 | 5/2008 | Dicarlo et al. | |
| 2008/0249483 A1 | 10/2008 | Slenker | |
| 2008/0281156 A1 | 11/2008 | Makower et al. | |
| 2008/0287918 A1 | 11/2008 | Rosenman et al. | |
| 2009/0030274 A1 | 1/2009 | Goldfarb et al. | |
| 2009/0093823 A1 | 4/2009 | Chang et al. | |
| 2009/0326450 A1 | 12/2009 | Ostrovsky et al. | |
| 2010/0010309 A1 | 1/2010 | Kitagawa | |
| 2010/0030113 A1 | 2/2010 | Morriss et al. | |
| 2010/0076269 A1 | 3/2010 | Makower et al. | |
| 2010/0099946 A1 | 4/2010 | Jenkins et al. | |
| 2010/0211007 A1 | 8/2010 | Lesch, Jr. et al. | |
| 2010/0217261 A1 | 8/2010 | Watson | |
| 2010/0262075 A1 | 10/2010 | Danitz et al. | |
| 2010/0331776 A1 | 12/2010 | Salahieh et al. | |
| 2011/0009700 A1 | 1/2011 | Ostrovsky et al. | |
| 2011/0040269 A1 | 2/2011 | Cline | |
| 2011/0112476 A1 | 5/2011 | Kauphusman et al. | |
| 2011/0190831 A1 | 8/2011 | Mafi et al. | |
| 2011/0218492 A1 | 9/2011 | McDaniel et al. | |
| 2011/0264134 A1 | 10/2011 | Drontle | |
| 2011/0313392 A1 | 12/2011 | Varghese et al. | |
| 2012/0046664 A1 | 2/2012 | McGuckin, Jr. et al. | |
| 2012/0101441 A1 | 4/2012 | Sargent, Jr. | |
| 2012/0162401 A1 | 6/2012 | Melder et al. | |
| 2012/0197240 A1 | 8/2012 | Smith et al. | |
| 2012/0238952 A1 | 9/2012 | Mitchell et al. | |
| 2012/0265055 A1 | 10/2012 | Melsheimer et al. | |
| 2013/0041314 A1 | 2/2013 | Dillon | |
| 2013/0046138 A1 | 2/2013 | McLawhorn | |
| 2013/0096384 A1 * | 4/2013 | Arai | 600/144 |
| 2013/0103004 A1 | 4/2013 | Gray et al. | |
| 2013/0238003 A1 | 9/2013 | Fischer et al. | |

FOREIGN PATENT DOCUMENTS

| | | |
|---|---|---|
| WO | 0170308 | 9/2001 |
| WO | 03001986 | 1/2003 |

OTHER PUBLICATIONS eyeMAX CCD Laparscopes [online brochure]. Richard Wolf GmbH [retrieved Nov. 15, 2013]. Retrieved from the Internet: URL: http://www.richard-wolf.com/uploads/media/A_658_Eyemax_GB_107.pdf. pp. 1-8.

eyeMAX Flexible LED Cystoscope [online brochure]. Richard Wilf GmbH [retrieved Nov. 15, 2013]. Retrieved from the internet: URL: http://www.richardwolfusa.com/fileadmin/images/content/USA_data/PDF_documents/Urology/Flexible_LED_Digital_Cystoscope_brochure_01312013.pdf. pp. 1-4.

Olympus Naso-laryngoscopes. Olympus. Retrieved from the internet: URL: www.olympuskeymed.com, pp. 1-3.

XprESS Multi-Sinus Dilation Tool. Instructions for Use, Entellus Medical, May 2011, pp. 1-7.

XprESS Multi-Sinus Dilation Tool Using Bending Tool. Instructions for Use, Entellus Medical, Sep. 2011, pp. 1-7.

A trial study of RhinoSleep for the diagnosis of sleep apnea. Psychiatry and Clinical Neurosciences. Jun. 2001, pp. 1-2.

E.G. Scan—Trans-nasal, disposable system for upper GI screening [online brochure]. SynMed Ltd. [retrieved Nov. 15, 2013]. Retrieved from the Internet: URL: http://www.synmed.co.uk/products/eg_scan/pdf/egscan.pdf.

Drug-induced Sleep Endoscopy webpage [online], Eric J. Kezirian [retrieved Nov. 14, 2013]. Retrieved from the internet: URL: http://www.sleep-doctor.com/surgical-treatment-overview/drug-induced-sleep-endoscopy/.

EyeMax webpage [online], Richard Wolf [retrieved Nov. 14, 2013]. Retrieved from the internet: URL: http://www.richard-wolf.com/en/human-medicine/visualisation/video-endoscopes/ccd-endoscopes.html.

* cited by examiner

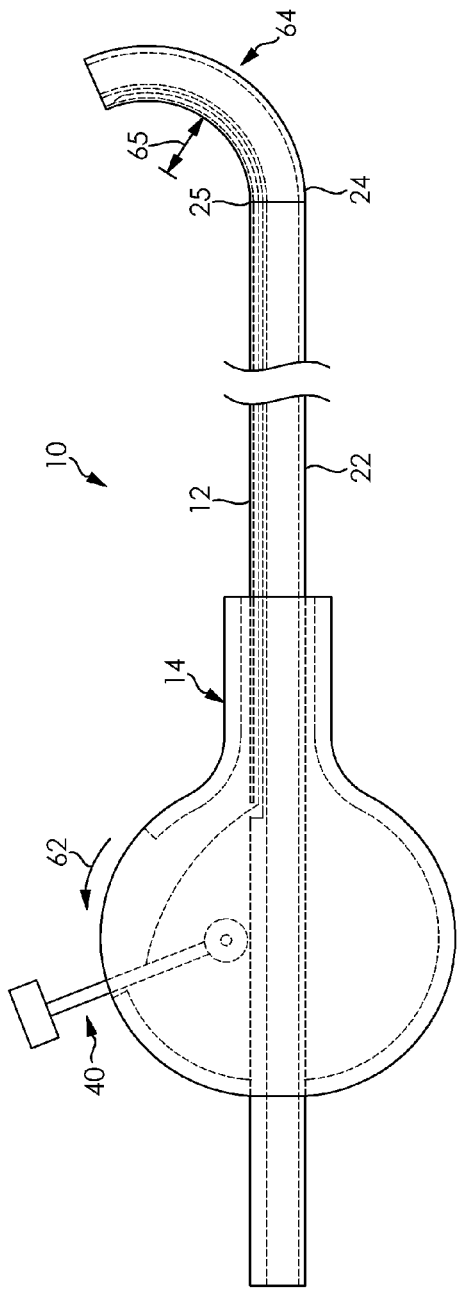
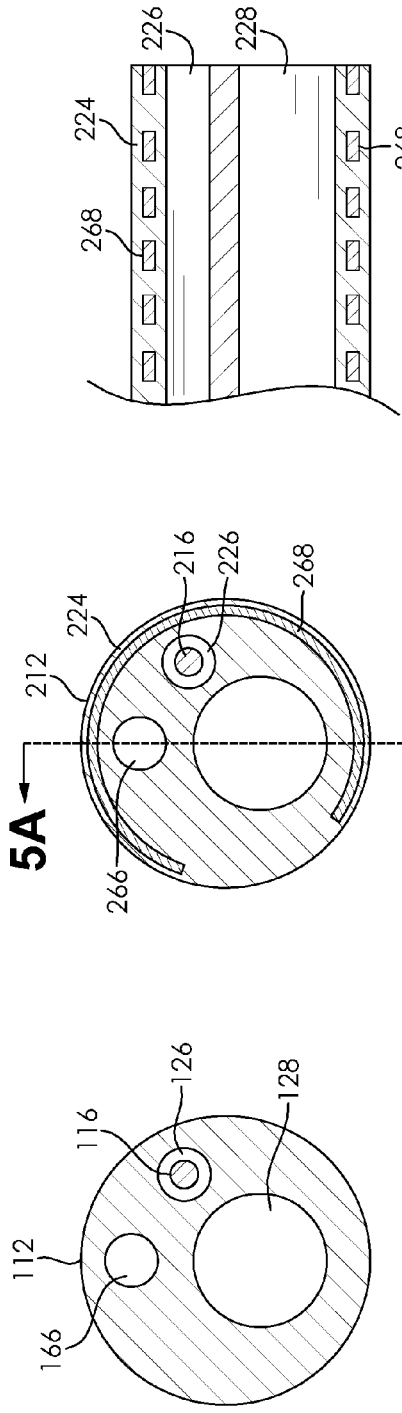

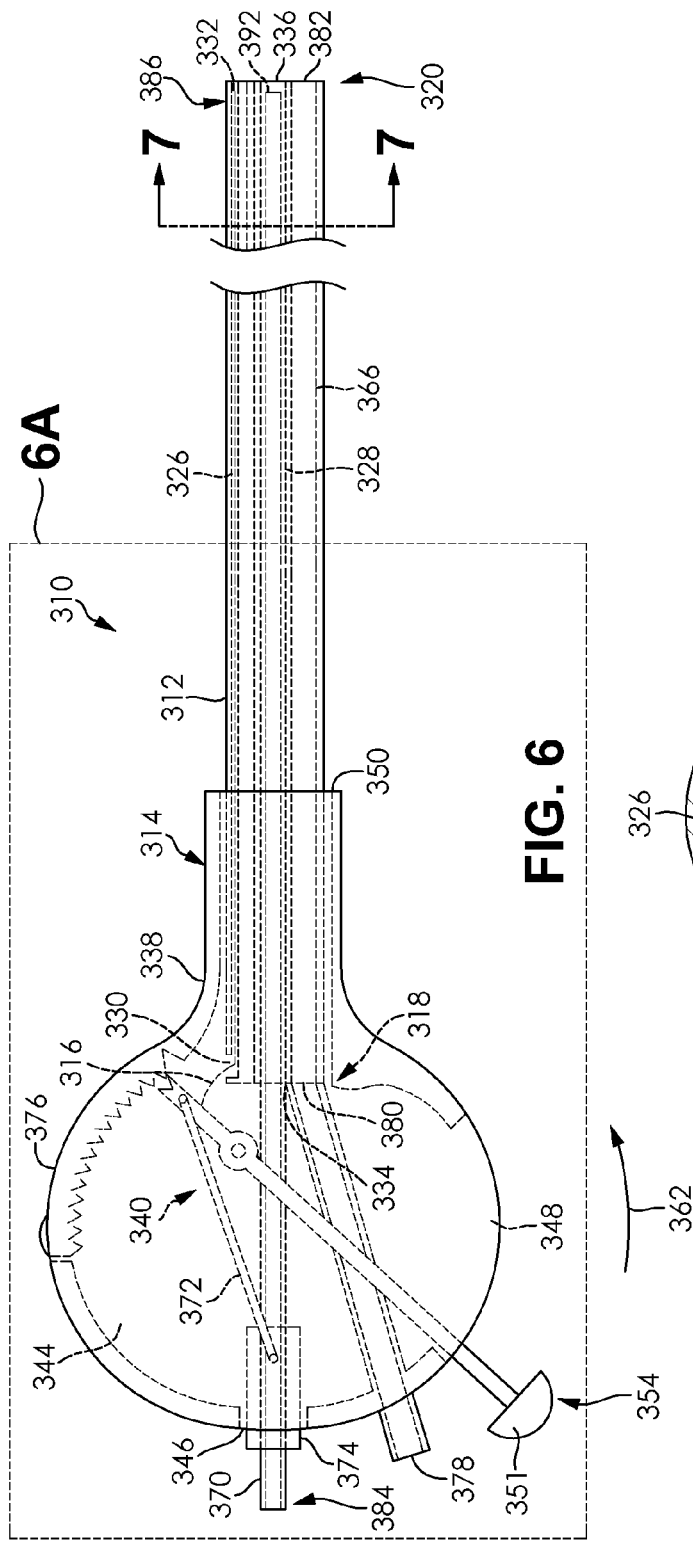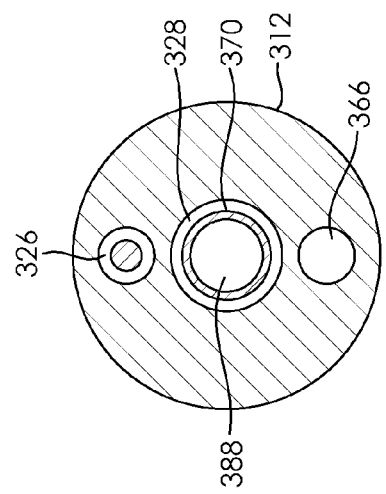

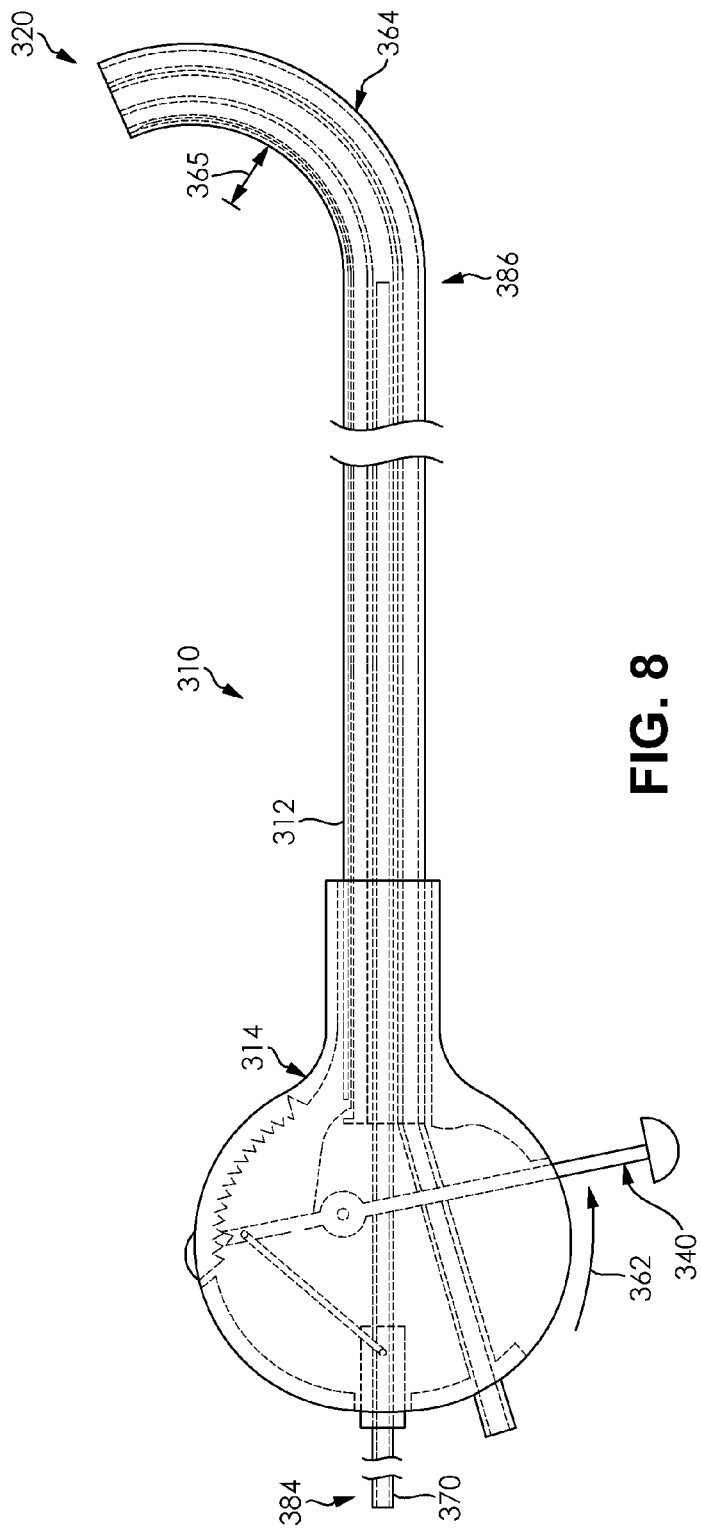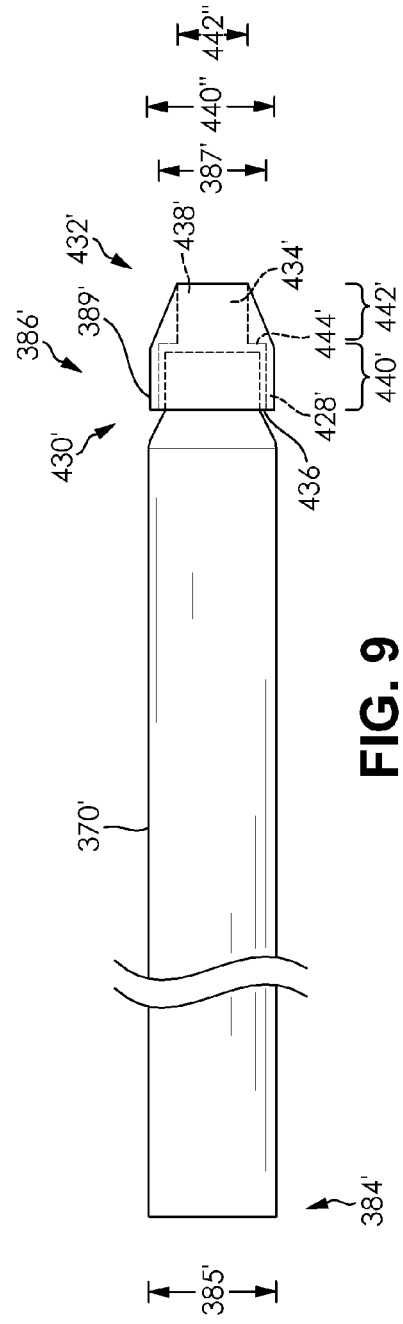
FIG. 8
FIG. 9

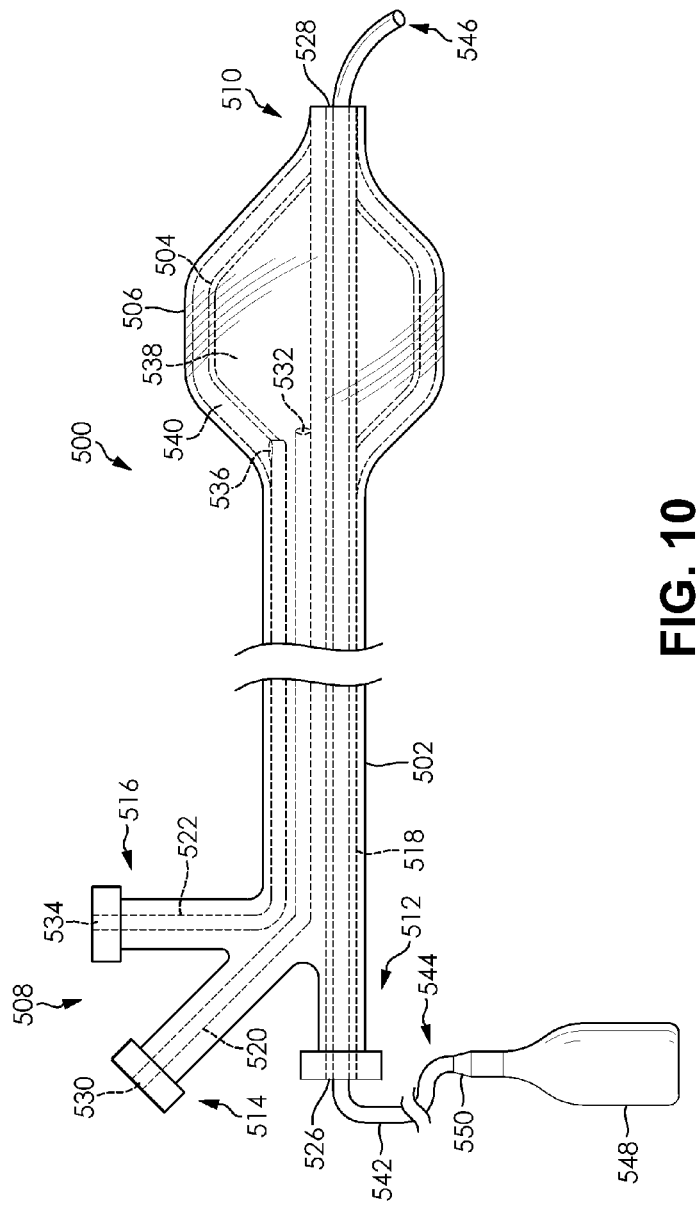
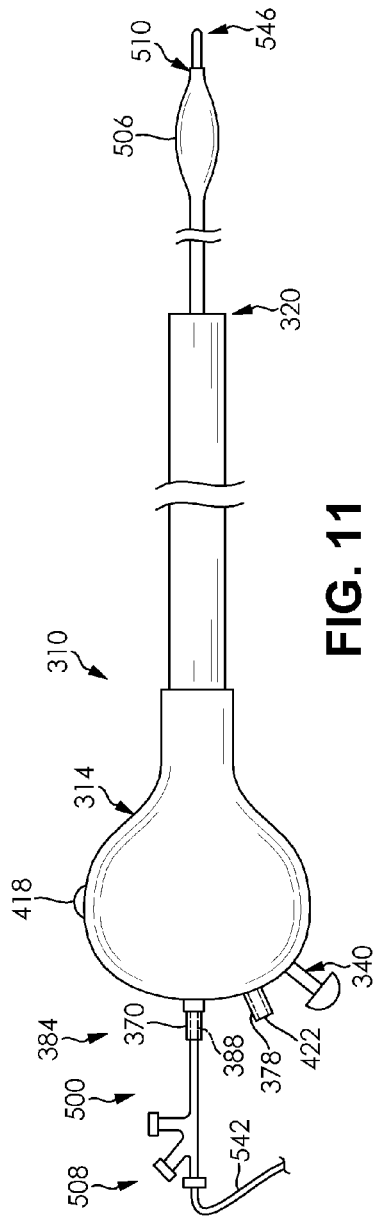
FIG. 10
FIG. 11

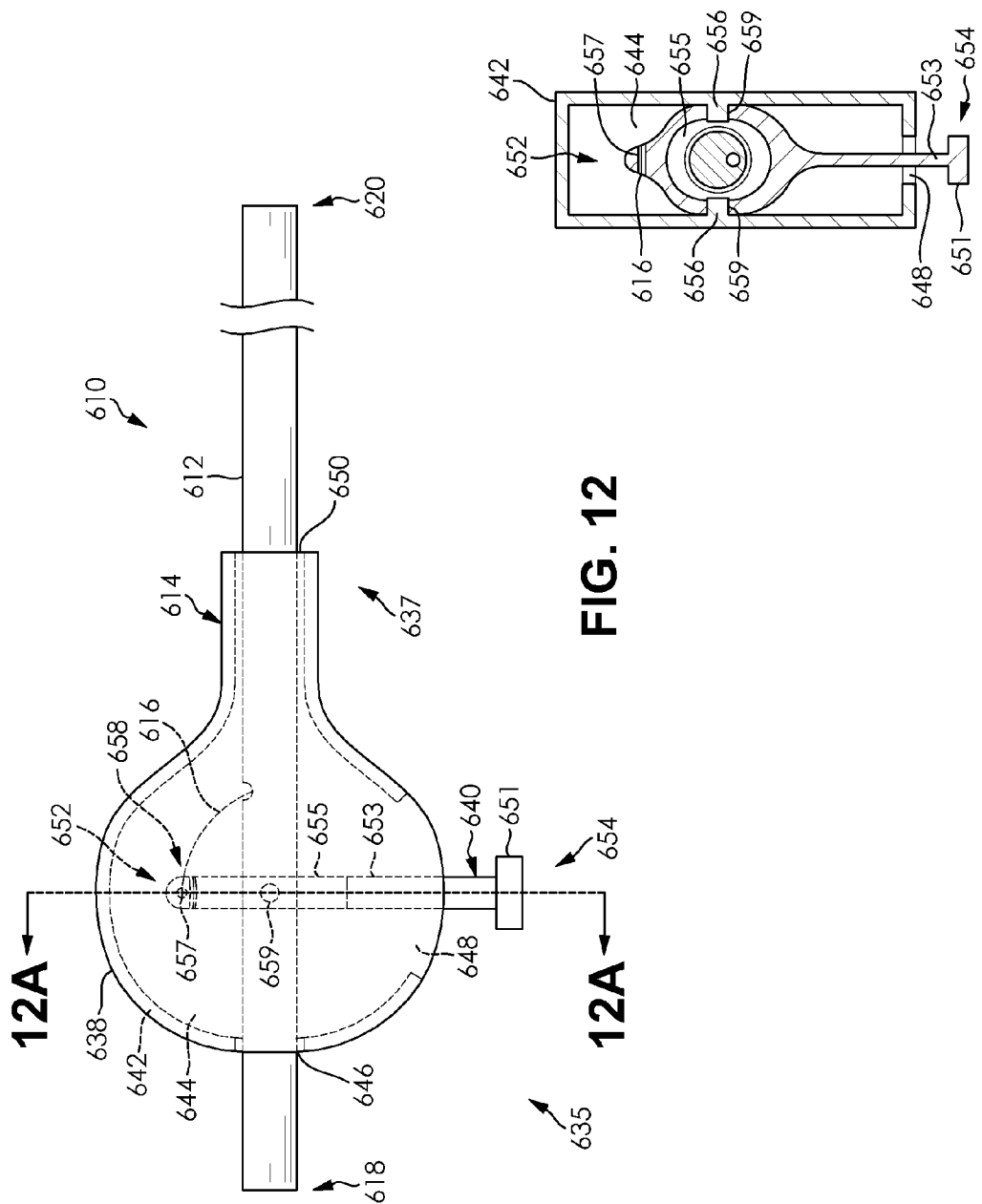

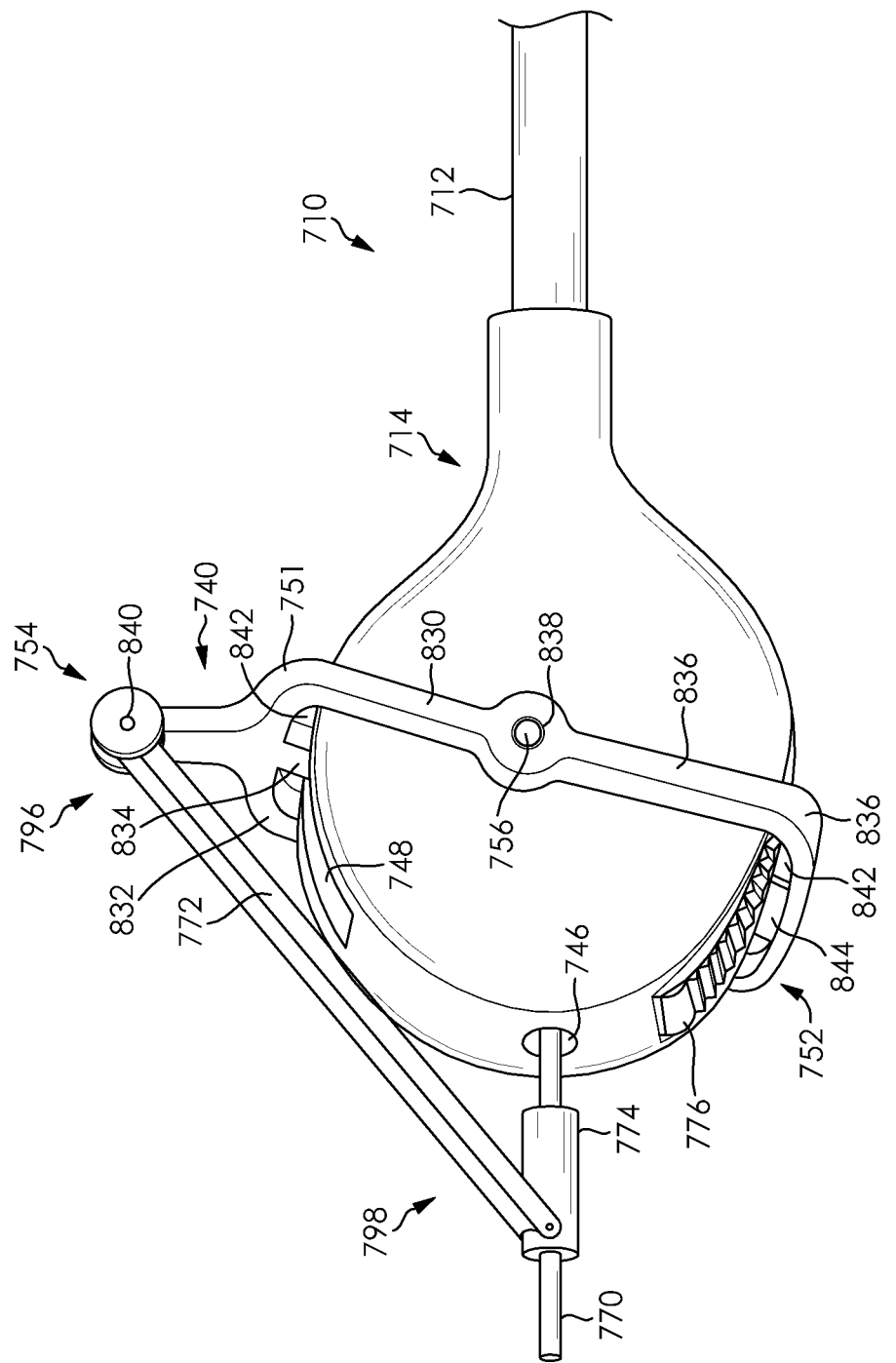

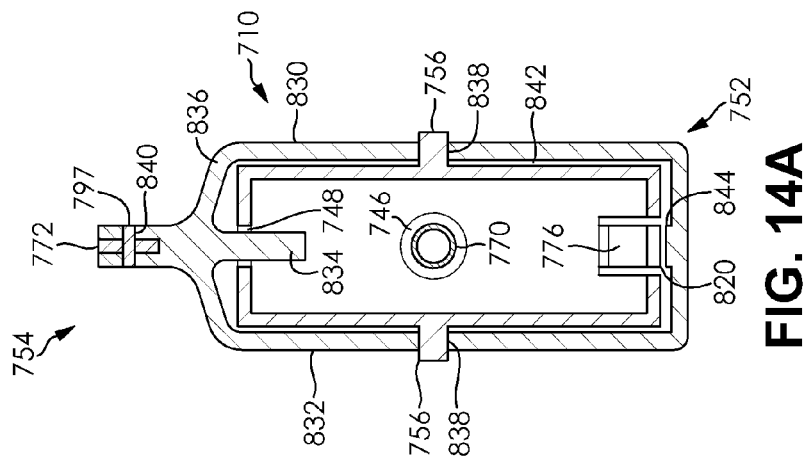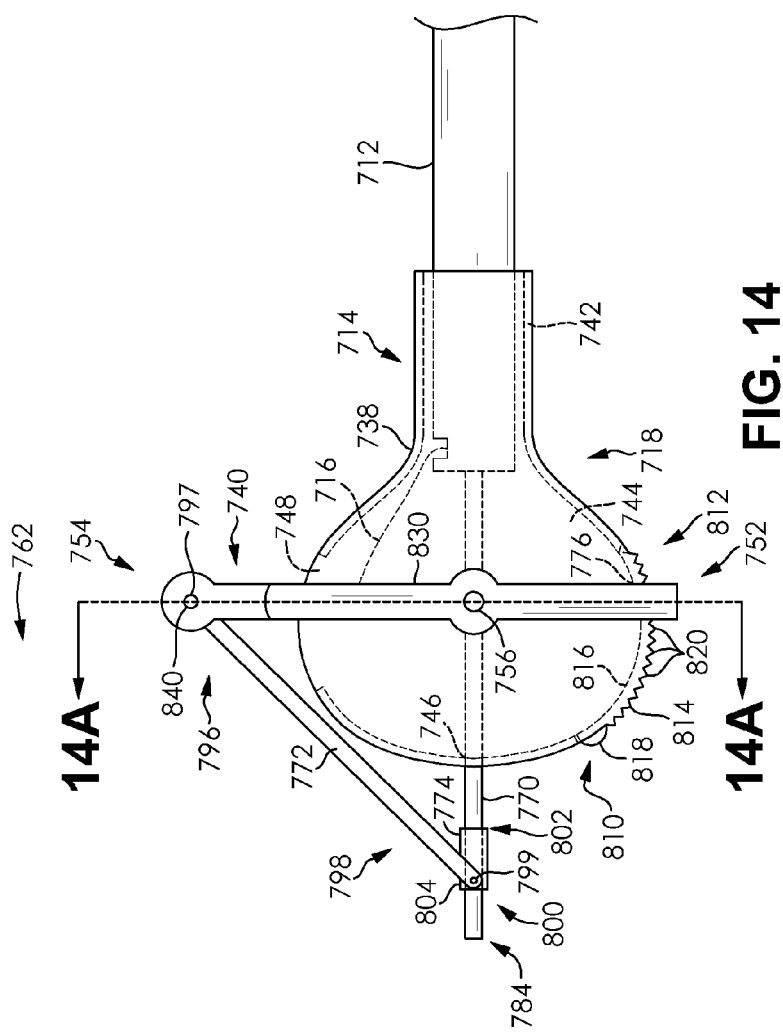

MEDICAL DEVICES FOR THE IDENTIFICATION AND TREATMENT OF BODILY PASSAGES

RELATED APPLICATIONS

This application claims the benefit of U.S. Provisional Application No. 61/704,652, filed Sep. 24, 2012. The entire contents of this related application is hereby incorporated into this disclosure by reference.

FIELD

The disclosure relates generally to medical devices. More particularly, the disclosure relates to medical devices and methods for the identification and treatment of bodily passages, such as sinus cavities.

BACKGROUND

It is sometimes necessary or otherwise desirable to identify and treat a bodily passage, such as a sinus cavity. For example, when sinus cavities become blocked, balloon sinuplasty—the dilation of the sinus using a balloon catheter—provides an alternative to radical surgical approaches to unblocking the sinus cavity. Conventional procedures utilize two separate devices to accomplish balloon sinuplasty, a rigid scope and a guiding catheter. The scope is utilized to locate the point of treatment and to provide visualization throughout the treatment process and the guiding catheter is used to guide a treatment device to the point of treatment.

Advancing a scope and guiding catheter separately towards a point of treatment has significant drawbacks because it increases the complexity of the procedure and the amount of time required to complete the procedure. For example, the individual performing the procedure must use both hands to manipulate the scope and guiding catheter. Doing so is awkward and, in some cases, requires an assistant to complete the procedure. Furthermore, due to the tortuous anatomy of many bodily passages, physicians generally must maintain a variety of scopes and guiding catheters that have many different angle configurations so that particular devices with appropriate configurations can be selected at the time of treatment.

Scopes have been developed that include a deflectable tip, which allows physicians to view various portions of a bodily passage during the performance of a procedure. However, these scopes still present significant drawbacks. For example, scopes that include deflectable tips are rigid in nature, which limits their ability to be navigated through the tortuous anatomy of a bodily passage. In addition, these scopes do not incorporate a flexible material or a mechanism for transitioning between a rigid configuration and a flexible configuration during the performance of a procedure. This prevents adjustment of the scope during the procedure such that the scope can be adapted to the anatomy of a bodily passage, for example, when it is desired to pass the scope through an opening defined by the bodily passage.

A need exists, therefore, for improved medical devices and methods for identifying and treating a bodily passage, such as a sinus cavity.

SUMMARY

Various exemplary medical devices are described.

A first exemplary medical device comprises an elongate member, a handle, a wire member, and a cannula. The elongate member has an elongate member proximal end, an elongate member distal end, and defines a first lumen and a second lumen. The handle is disposed on the elongate member and has an actuator moveable between an actuator first position and an actuator second position. The actuator has a first portion and a second portion. The wire member has a wire member first end attached to the first portion of the actuator and a wire member second end disposed within the first lumen and attached to the elongate member. The cannula has a cannula proximal end attached to the second portion of the actuator and a cannula distal end disposed within the second lumen. The cannula is moveable between a cannula first position when the actuator is in the actuator first position and a cannula second position when the actuator is in the actuator second position. In the cannula first position the cannula distal end is disposed at a first location. In the cannula second position the cannula distal end is disposed at a second location that is proximal to the first location. The elongate member is moveable between a substantially straight configuration when the actuator is in the actuator first position and a curved configuration when the actuator is in the actuator second position.

A second exemplary medical device comprises an elongate member, a handle, a wire member, and a cannula. The elongate member has an elongate member proximal end, an elongate member distal end, and defines a first lumen and a second lumen. The handle is disposed on the elongate member and has an actuator moveable between an actuator first position and an actuator second position. The actuator has a first portion and a second portion. The wire member has a wire member first end attached to the first portion of the actuator and a wire member second end disposed within the first lumen and attached to the elongate member. The cannula has a cannula proximal end attached to the second portion of the actuator and a cannula distal end disposed within the second lumen. The cannula is moveable between a cannula first position when the actuator is in the actuator first position and a cannula second position when the actuator is in the actuator second position. In the cannula first position the cannula distal end is disposed at a first location. In the cannula second position the cannula distal end is disposed at a second location that is proximal to the first location. The elongate member is moveable between a substantially straight configuration when the actuator is in the actuator first position and a curved configuration when the actuator is in the actuator second position. The cannula is formed of a substantially rigid material.

A third exemplary medical device comprises an elongate member, a handle, a wire member, and a cannula. The elongate member has an elongate member proximal end, an elongate member distal end, an elongate member first portion, an elongate member second portion, and defines a first lumen and a second lumen. The elongate member first portion extends from the elongate member proximal end towards the elongate member distal end to a location between the elongate member proximal end and the elongate member distal end. The elongate member second portion extends from the elongate member distal end towards the elongate member proximal end to a location between the elongate member proximal end and the elongate member distal end. The handle is disposed on the elongate member and has an actuator moveable between an actuator first position and an actuator second position. The actuator has a first portion and a second portion. The wire member has a wire member first end attached to the first portion of the actuator and a wire member second end disposed within the first lumen and attached to the elongate member. The cannula has a cannula proximal end attached to the second portion of the actuator and a cannula distal end disposed within the second lumen. The cannula is moveable between a cannula first position when the actuator is in the actuator first position and a cannula second position when the actuator is in the actuator second position. In the cannula first position the cannula distal end is disposed at a first location. In the cannula second position the cannula distal end is disposed at a second location that is proximal to the first location. The elongate member is moveable between a substantially straight configuration when the actuator is in the actuator first position and a curved configuration when the actuator is in the actuator second position. The elongate member first portion is formed of a first material and the elongate member second portion is formed of a second material. The second material is flexible relative to the first material. The cannula is formed of a substantially rigid material.

Additional understanding of the exemplary medical devices can be obtained by review of the detailed description, below, and the appended drawings.

BRIEF DESCRIPTION OF THE FIGURES

FIG. 3 is a side view of the medical device illustrated in FIG. 1 in a second configuration.

FIG. 4 is a sectional view of the distal end of an alternative elongate member of a medical device.

FIG. 5 is a sectional view of the distal end of a second alternative elongate member of a medical device.

FIG. 5A is a sectional view of the alternative elongate member illustrated in FIG. 5, taken along line 5A-5A.

FIG. 6 is a side view of a second exemplary medical device in a first configuration.

FIG. 7 is a sectional view of the medical device illustrated in FIG. 6, taken along line 7-7.

FIG. 8 is a side view of the medical device illustrated in FIG. 6 in a second configuration.

FIG. 9 is a side view of an alternative cannula of a medical device.

FIG. 10 is a side view of an exemplary catheter.

FIG. 11 is a side view of the catheter illustrated in FIG. 10 passed through a lumen of the second exemplary medical device illustrated in FIGS. 6, 6A, 7, and 8.

FIG. 12 is a side view of a third exemplary medical device.

FIG. 12A is a sectional view of the medical device illustrated in FIG. 12, taken along line 12A-12A.

FIG. 13 is a perspective view of the proximal end of a fourth exemplary medical device.

FIG. 14 is a side view of the proximal end of the medical device illustrated in FIG. 13.

FIG. 14A is a sectional view of the medical device illustrated in FIG. 14, taken along line 14A-14A.

DETAILED DESCRIPTION

The following detailed description and the appended drawings describe and illustrate various exemplary medical devices and methods of treatment. The description and drawings are exemplary in nature and are provided to enable one skilled in the art to make and use one or more exemplary medical devices and practice one or more of the methods described herein. They are not intended to limit the scope of the claims in any manner.

The use of "e.g.," "etc.," "for instance," "in example," and "or" and grammatically related terms indicates non-exclusive alternatives without limitation, unless otherwise noted. The use of "exemplary" refers to "an example of" and is not intended to convey a meaning of an ideal or preferred embodiment. As used herein, the terms "proximal" and "distal" are used to describe opposing axial ends of the particular elements or features being described. The use of "bodily passage" or "body passage" refers to any passage within the body of an animal, including, but not limited to, humans, and includes elongate passages. The term "sinus passage" refers to the nasal passages and includes, but is not limited to, eustachian tube(s), primary ostium, accessory ostium, airways, and/or an opening defined by a ventilation tube. The term "sinus cavity" refers to the frontal, ethmoid, sphenoid, and/or maxillary sinus. The use of "attached" refers to the fixed, releasable, or integrated association of two or more elements and/or devices, unless otherwise noted. Thus, the term "attached" includes releasably attaching or fixedly attaching, either permanently or temporarily, two or more elements and/or devices, unless otherwise noted.

FIGS. 1, 1A, 2, and 3 illustrate an exemplary medical device 10 comprising an elongate member 12, a handle 14, and a wire member 16.

Elongate member 12 can have any suitable outside diameter and any suitable length, and skilled artisans will be able to select a suitable outside diameter and length for an elongate member according to a particular embodiment based on various considerations, including the desired bodily passage within which a medical device is intended to be used. The inventors have determined that elongate members having an outside diameter between about 1 mm to about 7 mm are suitable. The inventors have also determined that elongate members having an outside diameter between about 3 mm to about 5 mm are suitable. Moreover, the inventors have determined that an elongate member having an outside diameter about 4 mm is suitable. The inventors have determined that elongate members having a length between about 10 cm to about 30 cm are suitable. The inventors have also determined that elongate members having a length between about 15 cm to about 28 cm are suitable.

Figure 1:
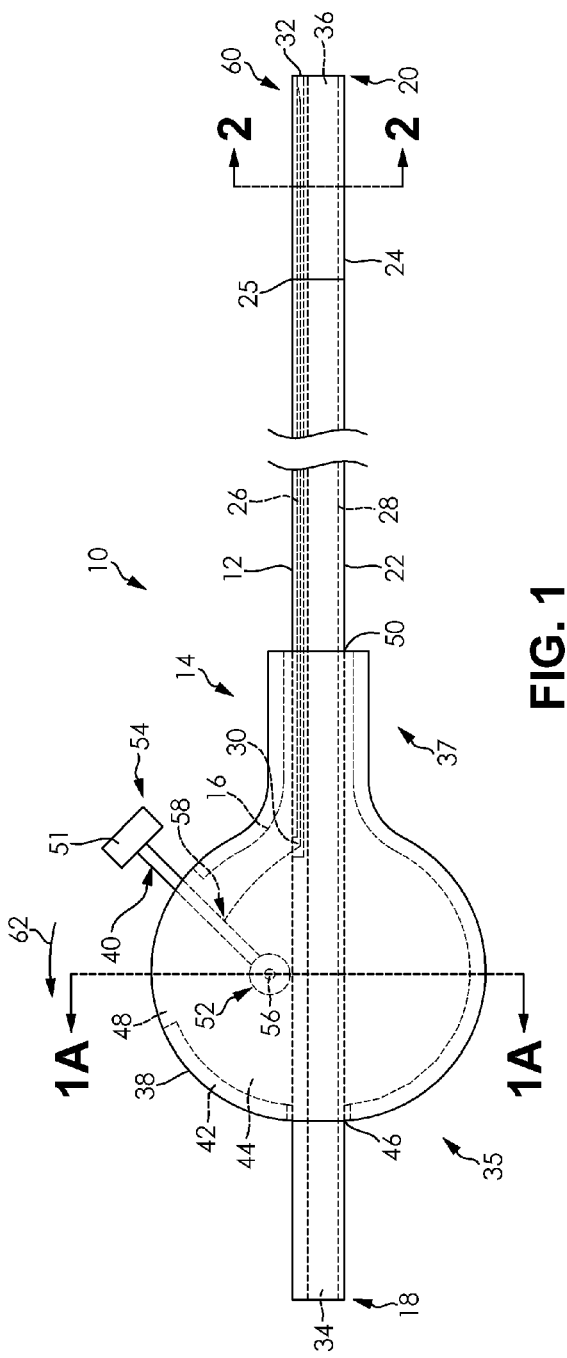
FIG. 1 is a side view of a first exemplary medical device in a first configuration.
Figure 2:
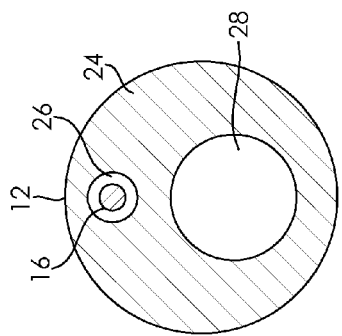
FIG. 2 is a sectional view of the medical device illustrated in FIG. 1, taken along line 2-2.
Figure 1A:
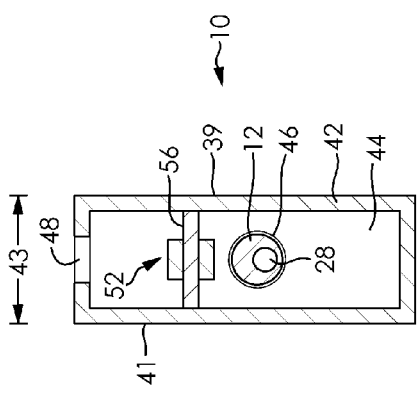
FIG. 1A is a sectional view of the medical device illustrated in FIG. 1, taken along line 1A-1A.

In the illustrated embodiment, elongate member 12 comprises an elongate member proximal end 18, an elongate member distal end 20, an elongate member first portion 22, an elongate member second portion 24, and defines a first lumen 26 and a second lumen 28. Elongate member first portion 22 extends from elongate member proximal end 18 towards elongate member distal end 20 to a location between elongate member proximal end 18 and elongate member distal end 20. Elongate member second portion 24 extends from elongate member distal end 20 towards elongate member proximal end 18 to a location between elongate member proximal end 18 and elongate member distal end 20. In the illustrated embodiment, the distal end of elongate member first portion 22 abuts the proximal end of elongate member second portion 24 at elongate member junction 25, which is located between elongate member proximal end 18 and elongate member distal end 20. Elongate member first portion 22 is formed of a first material that is rigid, or substantially rigid, and elongate member second portion 24 is formed of a second material that is flexible, or substantially flexible, relative to the material forming elongate member first portion 22. The second material that forms elongate member second portion 24 is different from the first material that forms elongate member first portion 22. Elongate member 12 is adapted to move between a straight, or substantially straight, configuration, as illustrated in FIG. 1, to a curved configuration, as illustrated in FIG. 3.

In the illustrated embodiment, elongate member junction 25 comprises a butt joint between elongate member first portion 22 and elongate member second portion 24. While a butt joint has been illustrated and described as attaching elongate member first portion 22 and elongate member second portion 24, any suitable method of attachment between an elongate member first portion and an elongate member second portion can be used. Skilled artisans will be able to select a suitable method of attachment between an elongate member first portion and an elongate member second portion according to a particular embodiment based on various considerations, including the nature of the materials forming the elongate member first portion and the elongate member second portion. Example methods of attachment considered suitable between an elongate member first portion and an elongate member second portion include, but are not limited to, a butt joint (as illustrated in FIGS. 1 and 3), a threaded joint, an overlapped joint, and any other method of attachment considered suitable for a particular application. It is considered advantageous to use a butt joint at least because this allows elongate member first portion and elongate member second portion to be contiguous to one another. Alternatively, an elongate member can be a single component such that a first portion and second portion are integral with one another.

Elongate member first portion 22 and elongate member second portion 24 can be formed of any suitable material and can be fabricated using any suitable method. Skilled artisans will be able to select suitable materials and methods of forming an elongate member first portion and an elongate member second portion according to a particular embodiment based on various considerations, including the desired flexibility of the elongate member. Example materials considered suitable for an elongate member first portion include, but are not limited to, biocompatible materials, materials that can be made biocompatible, metals such as stainless steel, titanium, nickel-titanium alloy (e.g., Nitinol), polymers, Pebax (Pebax is a registered trademark of Ato Chimie Corporation of Allee des Vosges, Courbevoie, France), nylon, polyethylene, polyurethane, silicone, coiled materials, and braided materials. Example materials considered suitable for an elongate member second portion include, but are not limited to, biocompatible materials, materials that can be made biocompatible, metals such as stainless steel, titanium, nickel-titanium alloy (e.g., Nitinol), polymers, Pebax, nylon, polyethylene, polyurethane, silicone, coiled materials, and braided materials. Example methods of manufacturing an elongate member include, but are not limited to, extrusion and molding processes.

For example, it is considered advantageous to form elongate member first portion 22 of a metal, such as stainless steel, and elongate member second portion 24 of a polymer at least because this provides rigidity to the elongate member 12 while also providing flexibility to elongate member second portion 24 such that it can define curve 64 as shown in FIG. 3.

Alternatively, an elongate member first portion and/or an elongate member second portion can be formed by layering material(s) along the length, or a portion of the length, of the elongate member first portion and/or elongate member second portion. For example, an elongate member first portion and/or an elongate member second portion can be formed of multiple layers of the same material or multiple layers of different materials. In instances where an elongate member first portion and/or an elongate member second portion are formed of multiple layers of different materials, each layer can comprise a different material, or a first layer can comprise a first material and a second layer can comprises a second material that is different than the first material. Any suitable combination of materials and/or layers of materials can be used to form an elongate member, an elongate member first portion, and/or an elongate member second portion.

While elongate member first portion 22 has been illustrated as having a length that is greater than the length of elongate member second portion 24, an elongate member first portion and/or an elongate member second portion can have any suitable length, and skilled artisans will be able to select a suitable length for an elongate member first portion and/or an elongate member second portion according to a particular embodiment based on various considerations, including the bodily passage within which a medical device is intended to be used. For example, when an elongate member includes an elongate member first portion and an elongate member second portion, the inventors have determined that elongate members that include an elongate member first portion that has a length between about 10 cm to about 30 cm are suitable. In addition, when an elongate member includes an elongate member first portion and an elongate member second portion, the inventors have determined that elongate members that include an elongate member first portion that has a length between about 15 cm to about 25 cm are also suitable. Moreover, when an elongate member includes an elongate member first portion and an elongate member second portion, the inventors have determined that elongate members that include an elongate member second portion that has a length between about 0.5 cm to about 3.5 cm are suitable. Furthermore, when an elongate member includes an elongate member first portion and an elongate member second portion, the inventors have determined that elongate members that include an elongate member second portion that has a length between about 1 cm to about 3 cm are also suitable.

While elongate member 12 has been described and illustrated as having an elongate member first portion 22 formed of a first material and an elongate member second portion 24 formed of a second, different, material, an elongate member can be formed of any suitable number of portions formed of any suitable number of materials, and skilled artisans will be able to select a suitable number of portions and materials to form an elongate member according to a particular embodiment based on various considerations, including the desired bodily passage within which a medical device is intended to be used. For example, alternative to a medical device including an elongate member having an elongate member first portion formed of a first material and an elongate member second portion formed of a second, different, material, an elongate member can be formed of the same material along its entire length, of different forms and/or compositions of the same material along its entire length, or a portion thereof, or formed of a plurality of different materials, each having a portion defined along the length of the elongate member. It is considered advantageous to form an elongate member, or portion thereof (e.g., elongate member first portion, elongate member second portion), of a braided material to add torsional strength to the elongate member and provide torquability of the elongate member during use. It is also considered advantageous to form an elongate member, or portion thereof (e.g., elongate member first portion, elongate member second portion), of a coiled material to provide kink-resistance. Optionally, an elongate member, or portion thereof (e.g., elongate member first portion, elongate member second portion), can be formed of both of a braided material and coiled material, to add torsional strength to the elongate member, provide torquability of the elongate member during use, and to provide kink-resistance.

For example, an elongate member can be a single continuous component such that an elongate member first portion and an elongate member second portion are integral with one another (e.g., junction 25 is omitted) and elongate member is formed of a single continuous material along its length. The material forming the elongate member can have a hardness that changes from the elongate member proximal end to the elongate member distal end (e.g., durometer hardness). The hardness at the elongate member proximal end, or elongate member first portion, can have a first quantity and the hardness at the elongate member distal end, or elongate member second portion, can have a second quantity that is different than the first quantity such that the elongate member distal end, or elongate member second portion, is more flexible than the elongate member proximal end, or elongate member first portion. Thus, the hardness at the elongate member proximal end, or elongate member first portion, can be greater than the hardness at the elongate member distal end, or the second portion of the elongate member, to provide rigidity along the elongate member proximal end, or elongate member first portion, and flexibility along the elongate member distal end, or elongate member second portion.

First lumen 26 extends from a first lumen first opening 30 disposed distal to elongate member proximal end 18 along the length of elongate member 12 between elongate member proximal end 18 and elongate member distal end 20 and a first lumen second opening 32 disposed at elongate member distal end 20. Second lumen 28 extends from a second lumen first opening 34 disposed at elongate member proximal end 18 and a second lumen second opening 36 disposed at elongate member distal end 20.

The inclusion of second lumen 28 is considered advantageous at least because it allows for the introduction of one or more secondary devices through elongate member 12. Any suitable secondary device can be passed through an elongate member, and skilled artisans will be able to select a suitable secondary device according to a particular embodiment based on various considerations, including the desired treatment intended to be performed. Example devices considered suitable to pass through a lumen defined by an elongate member include, but are not limited to, catheters, balloon catheters, suction devices, graspers, cutting tools, illuminating members, optical fibers, cameras, chip-in-tip fiber optics, imaging devices, imaging fibers, and any other device considered suitable for a particular application. For example, an illuminating member can be passed through the lumen of an elongate member that comprises a light-emitting distal end, as described in more detail below.

While elongate member 12 has been illustrated and described as defining a first lumen 26 and a second lumen 28, an elongate member can define any suitable number of lumens having any suitable diameter, and skilled artisans will be able to select a suitable number of lumens and suitable diameters according to a particular embodiment based on various considerations, including the bodily passage within which the medical device is intended to be used and/or the devices being used in combination with the elongate member. Example number of lumens considered suitable include, but are not limited to, one, at least one, two, a plurality, three, four, and any other number considered suitable for a particular application. For example, it is considered advantageous for a lumen (e.g., second lumen 28) of an elongate member that is adapted to receive and allow one or more secondary devices to pass through the elongate member to have the largest suitable diameter. For example, second lumen 28 can have a diameter that is larger than any other lumen defined by elongate member (e.g., first lumen 26).

Any portion, or the entirety, of the elongate member 12, first lumen 26, second lumen 28, or any other lumen defined by an elongate member, can be lined and/or coated with any suitable material to reduce the coefficient of friction between the outer surface of the elongate member and the surface in which the outer surface is intended to, or may, contact, or the surface defining the lumen and the surface of a device being passed through the lumen. Any suitable lining and/or coating capable of reducing the coefficient of friction is considered suitable, and skilled artisans will be able to select a suitable lining and/or coating according to a particular embodiment based on various considerations, such as the bodily passage within which the medical device is intended to be used. A lining and/or coating can be included along any suitable portion, or the entirety, of the elongate member length. Example lubricious coatings considered suitable to reduce the coefficient of friction include, but are not limited to, polymers such as polyethylene (PE), polytetrafluoroethylene (PTFE), and any other polymer or substance having properties that result in the lowering of the coefficient of friction between two surfaces.

While first lumen first opening 30, first lumen second opening 32, second lumen first opening 34, and second lumen second opening 36 have been described and illustrated as positioned at particular locations on elongate member 12, the opening of a lumen can be positioned at any suitable location on, or along the length of, an elongate member. Skilled artisans will be able to select a suitable location to position a lumen opening according to a particular embodiment based on various considerations, including the desired bodily passage within which a medical device is intended to be used. Example positions considered suitable to locate an opening of a lumen on an elongate member include, but are not limited to, on the elongate member proximal end, along the length of an elongate member between the elongate member proximal end and the elongate member distal end, and on the elongate member distal end. For example, alternative to positioning a first lumen first opening along the length of an elongate member between the elongate member proximal end and the elongate member distal end, the first lumen first opening can be positioned on the elongate member proximal end. Alternative to positioning a first lumen second opening on the elongate member distal end, the first lumen second opening can be omitted and the first lumen can terminate proximal to the elongate member distal end and only comprise a first opening.

Handle 14 can be formed of any suitable material, and skilled artisans will be able to select a suitable material to form a handle according to a particular embodiment based on various considerations, including the desired bodily passage within which a medical device is intended to be used. Example materials considered suitable to form a handle include, but are not limited to, biocompatible materials, materials that can be made biocompatible, metals such as stainless steel, titanium, nickel-titanium alloy (e.g., Nitinol), polymers, Pebax, nylon, polyethylene, polyurethane, silicone, and braided materials.

In the illustrated embodiment, handle 14 is disposed along the length of elongate member 12 between elongate member proximal end 18 and elongate member distal end 20 and comprises a handle proximal end 35, a handle distal end 37, a housing 38, and an actuator 40. Housing 38 has a housing wall 42 that defines a housing cavity 44, a first housing opening 46, a second housing opening 48, and a third housing opening 50.

Each of the first housing opening 46, second housing opening 48, and third housing opening 50 extends through the housing wall 42 and provides access to housing cavity 44.

While handle 14 has been described and illustrated as disposed along the length of elongate member 12 between elongate member proximal end 18 and elongate member distal end 20, the handle of a medical device can be positioned at any suitable location on an elongate member. Skilled artisans will be able to select a suitable position for a handle on an elongate member according to a particular embodiment based on various considerations, including the structural arrangement of the handle and materials forming the elongate member. Example locations considered suitable to position a handle on an elongate member include, but are not limited to, positioning the handle on the elongate member proximal end, positioning the handle on an elongate member such that the elongate member proximal end is disposed within a cavity defined by the handle, and positioning the handle on an elongate member such that the elongate member proximal end is disposed on the handle distal end.

Positioning handle 14 along the length of elongate member 12 between elongate member proximal end 18 and elongate member distal end 20 is considered advantageous at least because it provides stability of medical device 10 during use and positions a portion of elongate member 12 proximal to handle 14 such that the introduction of one or more secondary medical devices can be accomplished.

In the illustrated embodiment, the handle proximal end 35 comprises a handle first side 39, an opposably positioned handle second side 41, and a handle thickness 43. Each of the handle first side 39 and handle second side 41 has a round, or substantially round, perimeter that tapers to handle distal end 37, which has a tubular configuration. This structural arrangement is considered advantageous at least because it allows one-handed operation of medical device 10 such that a user can both maintain control of the medical device during use and activate actuator 40 to move elongate member 12 between a straight, or substantially straight, configuration, to a curved configuration, as described herein. While handle 14 has been described and illustrated as having a particular structural arrangement, any suitable structural arrangement of a handle is considered suitable for a medical device. Skilled artisans will be able to select a suitable structural arrangement for a handle of a medical device according to a particular embodiment based on various considerations, including the structural arrangement of the actuator being used. Example alternative structural arrangements considered suitable for a handle include, but are not limited to, linear, round, elliptical, oblong, and any other structural arrangement considered suitable for a particular application.

Actuator 40 is moveable between an actuator first position, as shown in FIG. 1, and an actuator second position, as shown in FIG. 3. Movement of actuator 40 between the actuator first position and the actuator second position results in movement of elongate member 12 between a first straight, or substantially straight, configuration, as shown in FIG. 1, and a curved configuration, as shown in FIG. 3 and as described in more detail below. Any suitable actuator can be used in a medical device, and skilled artisans will be able to select a suitable actuator to include in a medical device according to a particular embodiment based on various considerations, including the desired radius of curvature defined by an elongate member when the actuator is moved between an actuator first position and an actuator second position. Example actuators considered suitable for a medical device include, but are not limited to, linear actuators, rotatable actuators, pivotable actuators, and electro-mechanical actuators.

As shown in the illustrated embodiment, an example of a suitable actuator 40 is lever 51 that comprises a lever first end 52 disposed within the housing cavity 44 and a lever second end 54 disposed outside of housing cavity 44. Lever 51 extends through second housing opening 48. Lever first end 52 is pivotably attached to housing wall 42 by pin 56 that extends through an aperture defined by the wall of lever 51 such that lever 51 can move within second housing opening 48 between a lever first position and a lever second position. FIG. 1 illustrates lever 51 in the lever first position and FIG. 3 illustrates lever 51 in the lever second position.

While pin 56 has been illustrated and described as providing pivotable attachment between lever 51 and housing 38, any suitable method of attachment between an actuator (e.g., lever) and a housing can be used. Skilled artisans will be able to select a suitable method of attachment between an actuator and a housing according to a particular embodiment based on various considerations, including the materials forming the actuator and the housing. An example method of attachment considered suitable between an actuator and a housing includes, but is not limited to, using a threaded attachment device (e.g., screw), a shaft, and any other method of attachment considered suitable for a particular application.

Wire member 16 can be formed of any suitable material, and skilled artisans will be able to select a suitable material for a wire member of a medical device according to a particular embodiment based on various considerations, including the material that forms an elongate member of the medical device. Example materials considered suitable to form a wire member include, but are not limited to, biocompatible materials, materials that can be made biocompatible, braided materials, polymers, nylon, and metals such as stainless steel, titanium, and nickel-titanium alloy (e.g., Nitinol).

In the illustrated embodiment, wire member 16 comprises a wire member first end 58 and a wire member second end 60. Wire member first end 58 is attached to a portion of actuator 40. In the illustrated embodiment, wire member first end 58 is attached to lever 51 between lever first end 52 and lever second end 54. Wire member second end 60 is attached within first lumen 26 proximal to elongate member distal end 20. In the illustrated embodiment, wire member first end 58 is bonded (e.g., using an adhesive, welding, fusing) to lever 51.

While wire member first end 58 has been described and illustrated as bonded to lever 51, a wire member can be connected to an actuator (e.g., lever 51) using any suitable method of attachment, and skilled artisans will be able to select a suitable method of attachment between a wire member and an actuator according to a particular embodiment based on various considerations, including the materials forming the wire member and the actuator. Example methods of attachment are described herein and below with respect to FIGS. 15, 16, and 17. These examples, however, are not limiting in nature and any suitable method of attachment between a wire member and an actuator can be used.

Figure 15:
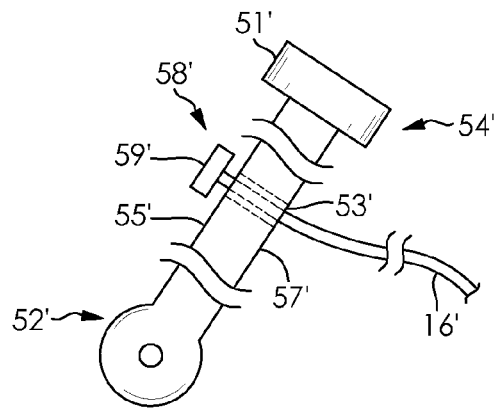
FIG. 15 is a side view of a first alternative method of connecting a wire member to an actuator.

FIG. 15 illustrates a first alternative method for attaching a wire member to an actuator. In the illustrated embodiment, the wall of lever 51' defines an aperture 53' that extends through lever 51' between the lever first end 52' and lever second end 54' and from a first opening on a lever first side 55' to a second opening on a lever second side 57'. Wire member first end 58' comprises a stopper 59' that has an outside diameter that is greater than the diameter of aperture 53'. Wire member 16' is disposed through aperture 53' until stopper 59' contacts lever 51' preventing, or eliminating, further movement of wire member 16' through lever 51'.

Stopper 59' can comprise any suitable structure and/or material and be attached to wire member 16' using any suitable method, and skilled artisans will be able to select a suitable structure and/or material and a suitable method of attachment between a stopper and a wire member according to a particular embodiment based on various considerations, including the materials forming the wire member. For example, a stopper can comprise a separate element attached to a wire member (e.g., a separate element crimped onto wire member). Alternatively, a stopper can be integral with a wire member.

Figure 16:
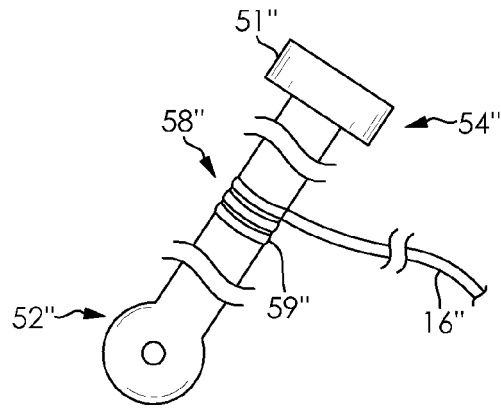
FIG. 16 is a side view of a second alternative method of connecting a wire member to an actuator.

FIG. 16 illustrates a second alternative method for attaching a wire member to an actuator. In the illustrated embodiment, wire member first end 58" is wrapped around lever 51" between lever first end 52" and lever second end 54". At 59" wire member 16" is attached to lever 51" and/or to a portion of the wire member 16" that is wrapped around lever 51". A wire member can be wrapped around an actuator (e.g., lever 51") any suitable number of times and any suitable method of attachment between a wire member and an actuator and/or a portion of the wire member wrapped around the actuator can be used. Skilled artisans will be able to select a suitable number of times to wrap a wire member around an actuator and a suitable method of attachment between a wire member and an actuator and/or a portion of the wire member that is wrapped around the actuator according to a particular embodiment based on various considerations, including the material(s) forming the wire member. For example, a wire member can be wrapped around an actuator one, at least one, two, a plurality, three, four, five, six, seven, and any other number of times considered suitable for a particular application. Example methods of attachment considered suitable between a wire member and an actuator and/or a portion of the wire member that is wrapped around an actuator include, but are not limited to, using an adhesive, welding, fusing, knotting the wire member, and any other method of attachment considered suitable for a particular application.

Figure 17:
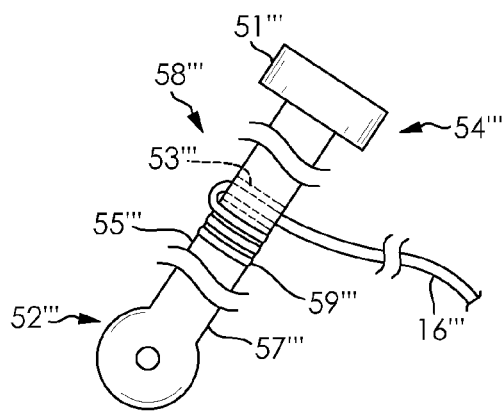
FIG. 17 is a side view of a third alternative method of connecting a wire member to an actuator.

FIG. 17 illustrates a third alternative method for attaching a wire member to an actuator. In the illustrated embodiment, the wall of lever 51'" defines an aperture 53'" that extends through lever 51'" between the lever first end 52'" and lever second end 54'" and from a first opening on a lever first side 55'" to a second opening on a lever second side 57'". Wire member 16'" is passed through aperture 53'" and is wrapped around lever 51'". At 59'" wire member 16'" is attached to lever 51'" or to a portion of the wire member 16'" that is wrapped around lever 51'". A wire member can be wrapped around an actuator (e.g. lever 51'") any suitable number of times and any suitable method of attachment between a wire member and an actuator and/or a portion of the wire member wrapped around the actuator can be used, as described herein.

While wire member second end 60 has been illustrated and described as attached within first lumen 26 proximal to elongate member distal end 20, a wire member second end can be attached at any suitable point along the length of a lumen defined by an elongate member using any suitable method of attachment. Skilled artisans will be able to select a suitable point to attach a wire member second end within a lumen defined by an elongate member and a suitable method of attachment according to a particular embodiment based on various considerations, including the axial length of the elongate member and/or the radius of curvature desired to be achieved by the elongate member. For example, alternative to wire member second end 60 being attached within first lumen 26 proximal to elongate member distal end 20, a wire member second end can be attached within a first lumen at the elongate member distal end, at the distal end, outside of a lumen defined by the elongate member distal end, or proximal to the elongate member distal end between the elongate member proximal end and the elongate member distal end. Example methods of attachment between a wire member and an elongate member considered suitable including, but are not limited to, using an adhesive, welding, fusing (e.g., heat fusing), crimping a stopper on the wire member second end, and any other method of attachment considered suitable for a particular application. For example, a wire member second end can comprise a stopper that has an outside diameter that is greater than the inside diameter of a portion of the lumen in which the wire member is disposed (e.g., lumen can taper along its length, lumen can define a shoulder along its length, lumen can define a protuberance along its length). Wire member second end can be disposed through the lumen in a manner that prevents proximal movement of the wire member second end when the stopper contacts the portion of the lumen that has a diameter that is less than that of the stopper. Thus, preventing, or eliminating, further movement of wire member second end through the lumen.

Any suitable structure and/or material can be attached to wire member (e.g., wire member second end) using any suitable method, and skilled artisans will be able to select a suitable structure and/or material and a suitable method of attachment between a stopper and a wire member according to a particular embodiment based on various considerations, including the materials forming the wire member. For example, a stopper can comprise a separate element attached to a wire member (e.g., a separate element crimped onto wire member). Alternatively, a stopper can be integral with a wire member.

In use, movement of lever 51 away from elongate member distal end 20, as shown by arrow 62, from the lever first position, as shown in FIG. 1, to the lever second position, as shown in FIG. 3, causes wire member 16 to move in a proximal, or substantially proximal, direction such that wire member first end 58 advances towards elongate member proximal end 18. This creates tension in wire member 16 that results in movement of wire member second end 60 and elongate member second portion 24 such that elongate member 12 moves from a straight, or substantially straight, configuration, as shown in FIG. 1, to a curved configuration, as shown in FIG. 3, in which elongate member 12 defines curve 64 at a radius of curvature 65. Movement of lever 51 towards elongate member distal end 20, in a direction opposite that of arrow 62, reduces, or eliminates, tension in wire member 16 and results in elongate member 12 returning to its straight, or substantially straight, configuration.

The radius of curvature 65 defined by elongate member 12 can be determined based upon at least the material(s) forming elongate member 12, the location of the lever second position, the length of elongate member 12, the length of wire member 16, and/or the axial length of second housing opening 48 as it relates to the length of handle 14. For example, if a smaller radius of curvature 65 is desired, the length of wire member 16 can be reduced as it relates to elongate member 12 and/or the axial length of second housing opening 48 can be increased as it relates to the length of handle 14. Alternatively, if a greater radius of curvature 65 is desired, the length of wire member 16 can be increased as it relates to elongate member 12 and/or the axial length of second housing opening 48 can be decreased as it relates to the length of handle 14. Alternatively, adjustment of lever 51 provides a mechanism for manipulating the radius of curvature 65 defined by elongate member 12. For example, advancing lever 51 from the lever first position in the proximal direction until the desired radius of curvature 65 is obtained and stopping proximal advancement of lever 51 can achieve a desired curve 64. It is considered advantageous to eliminate, or substantially eliminate, residual tension in wire member 16 when lever 51 is in the lever first position (e.g., lever 51 is near, or at, the distal end of second housing opening 48) at least because this configures elongate member 12 such that it is straight, or substantially straight, along its length.

Elongate member 12 can define curve 64 at any suitable radius of curvature 65, and skilled artisans will be able to select a suitable radius of curvature to define a curve according to a particular embodiment based on various considerations, including the desired bodily passage within which a medical device is intended to be used. Example radii considered suitable to define a curve include, but are not limited to, radii between about 1 mm to about 15 mm, and any other radius of curvature considered suitable for a particular application. The inventors have determined that elongate members that are capable defining a radius of curvature between about 3 mm to about 10 mm are suitable.

It is considered advantageous to provide an elongate member 12 that is adapted to move between a straight, or substantially straight, configuration and a curved configuration at least because this allows the medical device 10 to be advanced through tortuous bodily passages, such as sinus passages, and provides a mechanism for transitioning between a rigid, or substantially rigid, configuration and a curved configuration during the performance of a procedure. It is also considered advantageous to provide an elongate member 12 that is adapted to move between a straight, or substantially straight, configuration and a curved configuration at least because it provides a mechanism for using a single device to perform a procedure rather than conventional methods which require multiple devices (e.g., sheaths) to perform a procedure. For example, advancement of medical device 10 into a sinus cavity can be accomplished by advancing the elongate member distal end 20 in the straight, or substantially straight, configuration through a nasal passage (e.g., nostril). Once a sinus passage is located, elongate member 12 can be moved to the curved configuration by moving lever 51 to its second position such that elongate member distal end 20 can be positioned and advanced through the sinus passage and into the sinus cavity.

FIG. 4 illustrates a sectional view of the distal end of an alternative elongate member 112 of a medical device. Elongate member 112 is similar to elongate member 12 illustrated in FIGS. 1, 1A, 2, and 3, and described above, except as detailed below. Reference numbers in FIG. 4 refer to the same structural element or feature referenced by the same number in FIGS. 1, 1A, 2, and 3, offset by 100. Thus, elongate member 112 defines a first lumen 126 and a second lumen 128.

In the illustrated embodiment, a portion of wire member 116 is disposed within first lumen 126 and elongate member 112 defines a third lumen 166 that extends along the length of elongate member from a first opening on elongate member proximal end to a second opening on elongate member distal end. Inclusion of third lumen 166 is considered advantageous at least because it allows for one or more devices, such as secondary devices, to be passed through elongate member 112 (e.g., through second lumen 128 and/or third lumen 166). For example, a balloon catheter can be passed through second lumen 128 and an optical fiber can be passed through third lumen 166, as described below.

Any suitable secondary device can be passed through an elongate member, and skilled artisans will be able to select a suitable secondary device according to a particular embodiment based on various considerations, including the desired treatment intended to be performed. Example devices considered suitable to pass through a lumen defined by an elongate member include, but are not limited to, catheters, balloon catheters, suction devices, graspers, cutting tools, illuminating members, optical fibers, cameras, chip-in-tip fiber optics, imaging devices, imaging fibers, and any other medical device considered suitable for a particular application. Alternative to passing a secondary device through an elongate member, a secondary device can be preloaded within a lumen defined by an elongate member. For example, chip-in-tip fiber optics can be preloaded within a lumen defined by an elongate member.

FIGS. 5 and 5A illustrate sectional views of the distal end of a second alternative elongate member 212 of a medical device. Elongate member 212 is similar to elongate member 112 illustrated in FIG. 4, and described above, except as detailed below. Reference numbers in FIGS. 5 and 5A refer to the same structural element or feature referenced by the same number in FIG. 4, offset by 100. Thus, elongate member 212 defines a first lumen 226, a second lumen 228, and a third lumen 266 and a portion of wire member 216 is disposed within first lumen 226.

In the illustrated embodiment, alternative to forming elongate member second portion of a continuous material, elongate member second portion 224 comprises an embedded coil member 268. Inclusion of coil member 268 in an elongate member second portion 224 is considered advantageous at least because it reduces the likelihood of elongate member 212 kinking and/or buckling during use, for example, when elongate member 212 is moved between the first straight, or substantially straight, configuration and the second curved configuration.

Coil member 268 can extend along a portion or the entirety of the length of elongate member second portion 224 and/or elongate member 212. Example arrangements considered suitable for a coil member 268 include, but are not limited to, a coil member that extends from the elongate member proximal end to the elongate member distal end, a coil member that extends from the elongate member proximal end to the elongate member second portion, a coil member that extends from the elongate member proximal end to a point proximal to the elongate member second portion, a coil member that extends from a point distal to the elongate member proximal end to the elongate member distal end, a coil member that extends from a point distal to the elongate member proximal end to the elongate member second portion, a coil member that extends from a point distal to the elongate member proximal end to a point proximal to the elongate member second portion, a coil member that extends from the proximal end of the elongate member second portion to the elongate member distal end, a coil member that extends from a point distal to the proximal end of the elongate member second portion to the elongate member distal end, and a coil member that extends from a point distal to the proximal end of the elongate member second portion to a point proximal to the elongate member distal end. Alternatively, a coil member can be embedded within an elongate member, a first portion, and/or a second portion and disposed radially outward of, or about, one or more lumens defined by the elongate member. For example, a coil member can be embedded within an elongate member such that it is disposed radially outward of, or about, a first lumen, second lumen, and/or third lumen defined by the elongate member (e.g., first lumen 226, second lumen 228, third lumen 266).

Coil member 268 can be formed of any suitable material and have any suitable number of turns, and skilled artisans will be able to select a suitable material and number of turns for a coil member according to a particular embodiment based on various considerations, including the desired flexibility of the medical device. Example materials considered suitable for a coil member include but are not limited to, biocompatible materials, materials that can be made biocompatible, metals such as stainless steel, titanium, nickel-titanium alloy (e.g., Nitinol), and any other material considered suitable for a particular application. Example number of turns considered suitable for a coil member include, but are not limited to, one, at least one, two, a plurality, three, four, five, six, seven, eight, nine, ten, and any other number considered suitable for a particular application. In addition, each turn of a coil member can be positioned at any suitable length from an adjacent turn of the coil member. For example, a coil member can comprise equally width spaces between each turn of the coil member, or a coil member can comprise varying width spaces between each turn of the coil member.

In addition, while a single coil member has been described and illustrated herein, any suitable number of coil members can be used along any length of an elongate member, and skilled artisans will be able to select a suitable number of coil members according to a particular embodiment based on various considerations, including the desired bodily passage within which a medical device is intended to be disposed. Example number of coil members considered suitable include, but are not limited to, one, at least one, two, a plurality, three, four, and any other number considered suitable for a particular application.

Alternative to, or in combination with, including a coil member 268, an elongate member can comprise a braided material embedded within the elongate member, an elongate member first portion, and/or an elongate member second portion and disposed radially outward, or about, one or more lumens defined by the elongate member. For example, a coil member can be embedded within an elongate member such that it is disposed radially outward, or about, a second lumen defined by the elongate member (e.g., second lumen 228) and a braided material can be embedded within the elongate member such that it is disposed radially outward, or about, all of the lumens defined by the elongate member.

FIGS. 6, 6A, 7, and 8 illustrate another exemplary medical device 310. Medical device 310 is similar to medical device 10 illustrated in FIGS. 1, 1A, 2, and 3, and described above, except as detailed below. Reference numbers in FIGS. 6, 6A, 7, and 8 refer to the same structural element or feature referenced by the same number in FIGS. 1, 1A, 2, and 3, offset by 300. Thus, medical device 310 comprises an elongate member 312, a handle 314, and a wire member 316.

In the illustrated embodiment, medical device 310 comprises a cannula 370 that is partially disposed through elongate member 312 and handle 314. Handle 314 comprises an actuator 340, a locking mechanism 376, and defines a housing passageway 378 that extends from the exterior of housing 338 to the elongate member proximal end 318. Actuator 340 comprises a lever 351, a support arm 372, and a connecting member 374.

In the illustrated embodiment, elongate member 312 defines a third lumen 366 and does not include an elongate member first portion and an elongate member second portion formed of different materials. Rather, elongate member 312 is formed of the same material along its length. It is to be understood, however, that any suitable elongate member configuration, such as those described herein, can be used in combination with medical device 310. For example, alternative to elongate member 312 being formed of the same material along its length, an elongate material can comprise an elongate member first portion and an elongate member second portion, as described herein. Elongate member 312 has an elongate member proximal end 318, an elongate member distal end 320, and defines a first lumen 326, a second lumen 328, and a third lumen 366. The first lumen 326 extends from a first lumen first opening 330 positioned between elongate member proximal end 318 and elongate member distal end 320 to a first lumen second opening 332 on the elongate member distal end 320. The second lumen 328 extends from a second lumen first opening 334 on elongate member proximal end 318 to a second lumen second opening 336 on elongate member distal end 320. The third lumen 366 extends from a third lumen first opening 380 on elongate member proximal end 318 to a third lumen second opening 382 on elongate member distal end 320.

While first lumen first opening 330, first lumen second opening 332, second lumen first opening 334, second lumen second opening 336, third lumen first opening 380, and third lumen second opening 382 have been described and illustrated as positioned at particular locations on elongate member 312, the opening of a lumen can be positioned at any suitable location on, or along the length of, an elongate member. Skilled artisans will be able to select a suitable location to position an opening of a lumen according to a particular embodiment based on various considerations, including the structural arrangement of the handle of a medical device. Example positions considered suitable to locate a lumen opening on an elongate member include, but are not limited to, on the elongate member proximal end, along the length of the elongate member, on the elongate member distal end, and any other position considered suitable for a particular application, such as those described herein. For example, alternative to positioning a third lumen first opening on the elongate member proximal end, the third lumen first opening can be positioned along the length of the elongate member between elongate member proximal end and elongate member distal end.

While elongate member 312 has been described as formed of a single material along its length, an elongate member can be formed of one or more portions each formed of different materials, as described above. For example, alternative to elongate member 312 being formed of a single material along its length, the elongate member can comprise an elongate member first portion formed of a first material that is rigid, or substantially rigid, and an elongate member second portion formed of a second material, different from the first material, that is flexible, or substantially flexible, relative to the first material, as described herein.

In the illustrated embodiment, handle 314 is disposed on elongate member proximal end 318 such that elongate member proximal end 318 is positioned within housing cavity 344. This is considered advantageous at least because it provides stability of medical device 310 during use and limits the devices and/or structures positioned proximal to handle 314.

Cannula 370 can be formed of any suitable material and have any suitable length and outside diameter, and skilled artisans will be able to select a suitable material, length, and diameter for a cannula according to a particular embodiment based on various considerations, including the material(s) forming the elongate member and/or the structural arrangement of the elongate member. Example materials considered suitable to form a cannula include, but are not limited to, biocompatible materials, materials that can be made biocompatible, metals such as stainless steel, titanium, nickel-titanium alloy (e.g., Nitinol), polymers, rigid polymers, and any other material considered suitable for a particular application. It is considered advantageous to form cannula 370 of a rigid, or substantially rigid, material (e.g., metal, rigid polymer) at least because this provides rigidity to elongate member 312 during use. For example, a cannula can be formed of a material that is rigid relative to the material(s) that form the elongate member of a medical device (e.g., elongate member first portion, elongate member second portion). Example lengths considered suitable for a cannula include, but are not limited to, a length that is greater than the length of the elongate member, and a length that is greater than the distance between the first opening of the housing and the distal end of the elongate member.

Cannula 370 comprises a cannula proximal end 384, a cannula distal end 386, and defines a cannula lumen 388 that extends from a cannula first opening 390 on the cannula proximal end 384 to a cannula second opening 392 on the cannula distal end 386. Cannula 370 is slidingly disposed through a portion of housing 338 and a portion of elongate member 312. Cannula 370 is slidingly disposed through first housing opening 346 such that the cannula proximal end 384 is disposed proximal to housing 338 and outside of housing cavity 344 and cannula distal end 386 is slidingly disposed within second lumen 328 of elongate member 312. Thus, a portion of the length of cannula 370 is slidingly disposed within second lumen 328 of elongate member 312.

In the illustrated embodiment, lever 351 has a lever first end 352 disposed within the housing cavity 344, a lever second end 354 disposed outside of housing cavity 344, and defines a plurality of lever protuberances 394. Lever 351 is pivotably attached to housing wall 342 by pin 356, which is disposed between the lever first end 352 and the lever second end 354, and extends through an aperture defined by the wall of lever 351. The plurality of lever protuberances 394 is defined on a portion of lever second end 354 and each protuberance of the plurality of protuberances extends outwardly and away from lever 351. Lever 351 is adapted to move within housing second opening 348 between a lever first position and a lever second position. FIG. 6 illustrates lever 351 in the lever first position and FIG. 8 illustrates lever 351 in the lever second position.

Support arm 372 and connecting member 374 can be formed of any suitable material, and skilled artisans will be able to select a suitable material to form a support arm and/or connecting member according to a particular embodiment based on various considerations, including the materials that form cannula and/or lever. Example materials considered suitable for a support arm and/or connecting member include, but are not limited to, biocompatible materials, materials that can be made biocompatible, metals such as stainless steel, titanium, nickel-titanium alloy (e.g., Nitinol), polymers, Pebax, nylon, polyethylene, polyurethane, and silicone.

Support arm 372 has a support arm first end 396 and a support arm second end 398. Support arm first end 396 is pivotably attached to lever first end 352 by pin 397 that extends through a first aperture defined by the wall of support arm 372 and an aperture defined by the wall of lever 351. Support arm second end 398 is pivotably attached to connecting member 374 by pin 399 that extends through a second aperture defined by the wall of support arm 372.

Connecting member 374 has a connecting member proximal end 400, a connecting member distal end 402, and defines a connecting member lumen 404 that extends from a first opening on connecting member proximal end 400 to a second opening on connecting member distal end 402. Connecting member 374 is attached to cannula 370 between the cannula proximal end 384 and cannula distal end 386. Thus, connecting member 374 is slidingly disposed through first housing opening 346 and cannula 370 is attached to a portion of actuator 340.

Any suitable method of attachment is considered suitable between a cannula 370 and connecting member 374, and skilled artisans will be able to select a suitable method of attachment according to a particular embodiment based on various considerations, including the materials that form the cannula and/or connecting member. Example methods of attachment considered suitable between a cannula and a connecting member include, but are not limited to, using an adhesive, fusing, and/or welding. Optionally, connecting member 374 can be omitted from medical device 310 and support arm second end 398 can be pivotably attached directly to cannula 370.

While connecting member 374 has been described and illustrated as positioned between the cannula proximal end 384 and the cannula distal end 386, a connecting member can be positioned at any suitable location along the length of a cannula. Skilled artisans will be able to select a suitable position for a connecting member according to a particular embodiment based on various considerations, including the structural arrangement of the housing. Example locations considered suitable to position a connecting member on a cannula include, but are not limited to, positioning the connecting member on cannula distal end, and positioning the connecting member between cannula proximal end and cannula distal end.

While the cannula proximal end 384 and connecting member proximal end 400 have been illustrated as extending outside of housing cavity 344, the cannula and connecting member of a medical device can be positioned at any suitable location on a handle. Skilled artisans will be able to select a suitable location to position a cannula and connecting member of a medical device according to a particular embodiment based on various considerations, including the structural arrangement of the housing. For example, alternative to positioning the cannula proximal end 384 and connecting member proximal end 400 outside of housing cavity 344, a cannula proximal end and connecting member proximal end can be positioned flush with the housing wall, or within the housing cavity. It is considered advantageous to position the cannula proximal end 384 outside of housing cavity 344, or flush with housing wall 342, at least because this allows for one or more secondary devices to be passed through the cannula lumen 388.

Locking mechanism 376 is formed from a portion of housing 338 and comprises a locking mechanism first end 410, a locking mechanism second end 412, a locking mechanism exterior surface 414, and a locking mechanism interior surface 416, and defines a locking mechanism first protuberance 418 and a plurality of locking mechanism second protuberances 420. Locking mechanism first end 410 is free of housing 338 and locking mechanism second end 412 is pivotably attached to housing 338. Locking mechanism first protuberance 418 is defined on locking mechanism exterior surface 414 and extends outward and away from housing cavity 344. The plurality of locking mechanism second protuberances 420 is defined on locking mechanism interior surface 416 and each protuberance of the plurality of protuberances extends inward and towards housing cavity 344. In the illustrated embodiment, the plurality of locking mechanism second protuberances 420 is complementary to the plurality of lever protuberances 394.

Figure 6A:
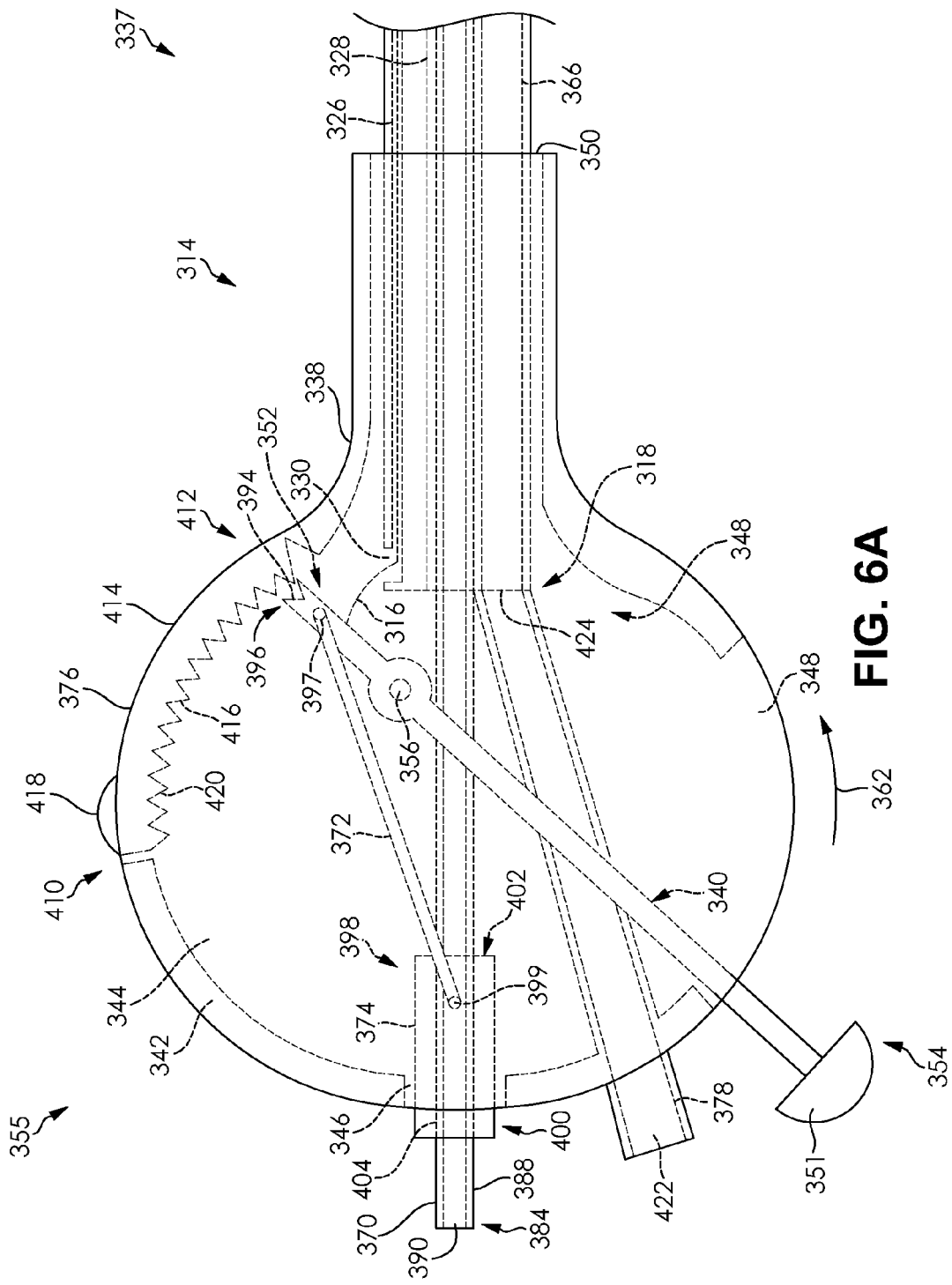
FIG. 6A is a magnified view of area 6A indicated in FIG. 6.

Locking mechanism 376 has a first position and a second position. In the first position, as shown in FIGS. 6, 6A, and 8, locking mechanism 376 is free of lever 351. In the second position (not shown), locking mechanism 376 is engaged with, or interacts with, lever 351 (e.g., plurality of lever protuberances). Locking mechanism 376 can be moved from the first position to the second position by applying a radially inward force on locking mechanism first protuberance 418 such that locking mechanism first end 410 moves inward into, or towards, housing cavity 344. This results in engagement of, or interaction between, the plurality of locking mechanism second protuberances 420 and the plurality of lever protuberances 394. In the second configuration, movement of lever 351 within second opening 348 is prevented, or substantially prevented. This is considered advantageous at least because it provides a mechanism for maintaining the position of lever 351 when elongate member 312 has defined a desired radius of curvature 365. Thus, lever 351 is adapted to be releasably fixed in the second position. The radius of curvature 365 defined by elongate member 312 can be adjusted by removing the radially inward force on locking mechanism first protuberance 418 and adjusting the position of lever 351 within second opening 348.

The inclusion of a locking mechanism 376 is considered advantageous at least because it provides a mechanism to prevent, or substantially prevent, movement of wire member 316, lever 351, connecting member 374, and cannula 370, when a desired radius of curvature 365 has been defined by elongate member 312. For example, it is considered advantageous to include a locking mechanism 376 at least because it allows the configuration of elongate member 312 to be fixed, or substantially fixed, when treatment is being performed (e.g., dilation of a bodily passage).

While locking mechanism 376 has been described and illustrated as providing a structure capable of maintaining the position of lever 351 in a second position, any suitable structural configuration capable of maintaining the position of an actuator (e.g., lever 351) is considered suitable for inclusion in a medical device. Skilled artisans will be able to select a suitable structural configuration to maintain the position of an actuator according to a particular embodiment based on various considerations, including the structural arrangement of the handle. In addition, while locking mechanism 376 has been described and illustrated as being formed from a portion of housing 338, a locking mechanism can be a separate element, or combination of elements, attached to the housing, or other portion, of a medical device.

Housing wall 342 defines housing passageway 378 that extends from a first passageway opening 422 on the exterior of housing 338 to a second passageway opening 424 in communication with the third lumen 366 of elongate member 312. It is considered advantageous to include passageway 378 to allow a user to pass one or more secondary devices through handle 314 and elongate member 312 (e.g., chip-in-tip fiber optics). Optionally, passageway 378 can be omitted from medical device 312 or more than one passageway can be defined by housing wall 342. Alternatively, multiple passageways can be defined by a housing such that each passageway is in communication with a lumen defined by an elongate member. This is considered advantageous at least because it provides a mechanism for passing one or more secondary devices (e.g., chip-in-tip fiber optics, illumination fibers, camera) through a handle and an elongate member.

In use, movement of lever 351 towards elongate member distal end 320, as shown by arrow 362, from the lever first position, as shown in FIGS. 6 and 6A, to the lever second position, as shown in FIG. 8, causes wire member 316 and support arm second end 398 to move in a proximal, or substantially proximal, direction. This results in cannula 370 being moved in the proximal direction within second lumen 328, tension in wire member 316, and movement of elongate member 312 from a straight, or substantially straight, configuration, as shown in FIG. 6, to a curved configuration, as shown in FIG. 8, in which elongate member 312 defines curve 364 at a radius of curvature 365. Movement of lever 351 towards the proximal end 384 of cannula 370, in a direction opposite that of arrow 362, advances cannula 370 towards elongate member distal end 320 within second lumen 328, reduces or eliminates tension in wire member 316, and results in elongate member 312 returning to its straight, or substantially straight, configuration.

In the illustrated embodiment, cannula 370 is moveable between a cannula first position and a cannula second position. In the cannula first position, as illustrated in FIG. 6, cannula distal end 386 is positioned at a first location at, or near, elongate member distal end 320. It is considered advantageous to position cannula distal end 386 at, or near, elongate member distal end 320 at least because this provides rigidity to elongate member 312 during use (e.g., when it is desired to pass medical device 310 through a bodily passage). In the cannula second position, as illustrated in FIG. 8, as a result of lever 351 being been moved from its lever first position to its lever second position, cannula distal end 386 is positioned at a second location, which is proximal to the first location. Movement of cannula 370 from the cannula first position to the cannula second position is considered advantageous at least because it allows elongate member 312 to move between a straight, or substantially straight, configuration in which elongate member 312 is rigid, or substantially rigid, to a curved configuration in which a portion of elongate member 312 is flexible, or substantially flexible.

Optionally cannula 370 can include an atraumatic tip on cannula distal end 386. It is considered advantageous to include an atraumatic tip on the cannula distal end 386 at least because it decreases the likelihood of wear and/or damage to elongate member 312 (e.g., lumen 328) when elongate member 312 is moved between a first straight, or substantially straight, configuration and a curved configuration. Including an atraumatic tip can be accomplished using any suitable method and using any suitable material, and skilled artisans will be able to select a suitable method of including an atraumatic tip and a suitable material to form an atraumatic tip according to a particular embodiment based on various considerations, including the materials that form an elongate member. Example methods of forming an atraumatic tip include, but are not limited to, forming a cannula distal end of a soft and/or flexible material, attaching a soft and/or flexible material to a cannula distal end, rounding a cannula distal end, perforating and/or cutting a cannula distal end to provide flexibility (e.g., using a cutting tool such as a laser), and spraying a cannula distal end with a lubricious material. Example materials considered suitable to form an atraumatic tip include, but are not limited to, biocompatible materials, materials that can be made biocompatible, polymers, metals, and any other material considered suitable for a particular application. For example, a polymer tip can be attached to a cannula distal end to reduce the likelihood of wear and/or damage to an elongate member during use.

FIG. 9 illustrates an alternative cannula of a medical device. In the illustrated embodiment, cannula proximal end 384' has a first cannula diameter 385' and cannula distal end 386' has a second cannula diameter 387' that is less than first cannula diameter 385'. An atraumatic tip 389' is disposed on cannula distal end 386'. Atraumatic tip 389' comprises an atraumatic tip wall 428', atraumatic tip proximal end 430' and an atraumatic tip distal end 432'. Atraumatic tip wall 428' defines a tapered atraumatic tip distal end 432' and an atraumatic tip aperture 434' that extends from an atraumatic tip first opening 436' on the atraumatic tip proximal end 430' to an atraumatic tip second opening 438' on the atraumatic tip distal end 432'. The atraumatic tip aperture 434' has an atraumatic tip first portion 440' that extends from atraumatic tip first opening 436' towards atraumatic tip second opening 438' and an atraumatic tip second portion 442' that extends from atraumatic tip first portion 440' to atraumatic tip second opening 438'. Atraumatic tip first portion 440' has an atraumatic tip first diameter 440" and atraumatic tip second portion 442' has an atraumatic tip second diameter 442". Atraumatic tip first diameter 440" is greater than atraumatic tip second diameter 442" and is equal to, substantially equal to, or less than, second cannula diameter 387'. This configuration is considered advantageous at least because it provides a friction fit between the atraumatic tip 389' and cannula 370'. In addition, it is considered advantageous to form atraumatic tip first diameter 440" greater than atraumatic tip second diameter 442" at least because this forms atraumatic tip shoulder 444' which provides a mechanical stop to advancement of cannula 370' through atraumatic tip 389'.

While atraumatic tip 389' has been illustrated and described as being attached to cannula distal end 386' via friction fit, any suitable method of attachment between a cannula and an atraumatic tip can be used, and skilled artisans will be able to select a suitable method of attachment between a cannula and an atraumatic tip according to a particular embodiment based on various considerations, including the material forming the cannula and/or atraumatic tip. Example methods of attachment considered suitable between a cannula and an atraumatic tip include, but are not limited to, fusing the atraumatic tip to the cannula (e.g., using heat), using an adhesive, and any other method of attachment considered suitable for a particular application.

Any suitable secondary device can be passed through the lumen and/or passageway of any of the medical devices described herein. For example, catheters, such as those described in co-pending application titled "Catheters and Methods for Identification and Treatment of Bodily Passages," filed on Nov. 25, 2011, having application Ser. No. 13/304,432, and hereby incorporated by reference into this disclosure in its entirety, can be used in combination with any of the medical devices described herein.

FIG. 10 illustrates an exemplary catheter 500 comprising an elongate main body 502, a first balloon 504, and a second balloon 506.

Elongate main body 502 has a main body proximal end 508, a main body distal end 510, and defines a secondary device port 512, a first inflation port 514, a second inflation port 516, a secondary device lumen 518, a first inflation lumen 520, and a second inflation lumen 522. Secondary device lumen 518 extends between a secondary device lumen first opening 526 in secondary device port 512 and a secondary device lumen second opening 528 on main body distal end 510. First inflation lumen 520 extends between a first inflation lumen first opening 530 in first inflation port 514 and a first inflation lumen second opening 532 located between main body proximal end 508 and main body distal end 510. Second inflation lumen 522 extends between a second inflation lumen first opening 534 in second inflation port 516 and a second inflation lumen second opening 536 located between main body proximal end 508 and main body distal end 510.

First balloon 504 is attached to main body distal end 510. The material of first balloon 504 and the portion of the exterior surface of main body 502 positioned within first balloon 504 define a first balloon inflation chamber 538. First balloon 504 is positioned on main body distal end 510 such that first inflation lumen second opening 532 is in communication with first balloon inflation chamber 538. With this structural arrangement, first balloon 504 is adapted to move between a deflated configuration and an inflated configuration as fluid is moved into and out of first balloon inflation chamber 538 via first inflation lumen 520 and first inflation lumen first opening 530.

Second balloon 506 is attached to main body distal end 510 such that it surrounds first balloon 504. The material of second balloon 506 and the portion of the exterior surface of main body 502 and the exterior surface of first balloon 504 define a second balloon inflation chamber 540. Thus, first balloon 504 is disposed within second balloon inflation chamber 540. Second balloon 506 is positioned on main body distal end 510 such that second inflation lumen second opening 536 is in communication with second balloon inflation chamber 540. With this structural arrangement, second balloon 506 is adapted to move between a deflated configuration and an inflated configuration as fluid is moved into and out of first balloon inflation chamber 538 and/or second balloon inflation chamber 540. Thus, a user can expand second balloon 506 either by inflating first balloon 504, inflating second balloon 506, or inflating both first balloon 504 and second balloon 506.

First balloon 504 can be moved from an inflated configuration to a deflated configuration by applying vacuum pressure to first inflation lumen 520 and removing the fluid disposed within first balloon inflation chamber 538. Second balloon 506 can be moved from an inflated configuration to a deflated configuration by applying vacuum pressure to second inflation lumen 522 and removing the fluid disposed within second balloon inflation chamber 540. FIG. 10 illustrates first balloon 504 and second balloon 506 in inflated configurations.

It is considered advantageous to provide a first balloon 504 and a second balloon 506 at least because it allows for catheter 500 to have two different maximum diameters in the inflated configuration. For example, first balloon 504 can be advanced to an inflated configuration (e.g., a diameter of 5 mm) and second balloon 506 can be left deflated, or both first balloon 504 and second balloon 506 can be advanced to an inflated configuration providing a greater diameter (e.g., a diameter of 7 mm) than that provided if only first balloon 504 was advanced to an inflated configuration. While particular inflated balloon diameters have been described, a balloon can be included that can achieve any suitable outside diameter in the inflated configuration, and skilled artisans will be able to select a suitable outside diameter for a balloon according to a particular embodiment based on various considerations, including the bodily passage intended to be treated. Example outside diameters considered suitable for a balloon include, but are not limited to, diameter between about 1 mm to about 10 mm. The inventors have determined that balloons having an inflated diameter between about 3 mm to about 10 mm are suitable. In addition, the inventors have determined that balloons having an inflated diameter about 7 mm are suitable.

In the illustrated embodiment, an optical fiber 542 is disposed through secondary device lumen 518. Optical fiber 542 extends between an optical fiber proximal end 544 and an optical fiber distal end 546 and defines a light path extending through its length that allows axially-directed light to emanate from optical fiber distal end 546. Optical fiber proximal end 544 is adapted to be operatively connected or attached to a light source 548. Optical fiber distal end 546 is free to move axially through secondary device lumen 518 such that it can be disposed proximal to main body proximal end 508 or main body distal end 510, distal to main body proximal end 508 or main body distal end 510, or disposed at, or near, main body proximal end 508 or main body distal end 510.

Any suitable optical fiber 542 can be used in combination with catheter 500 and/or any of the medical device described herein, and skilled artisans will be able to select a suitable optical fiber according to a particular embodiment based on various considerations, including the desired bodily passage within which a medical device is intended to be disposed. Example optical fibers considered suitable include, but are not limited to, commercially available optical fibers such as plastic optical fibers and glass optical fibers, with or without cladding.

Optical fiber 542 can have any suitable length, and skilled artisans will be able to select a suitable length for an optical fiber according to a particular embodiment based on various considerations, the location of the bodily passage intended to be identified and/or treated. An example length considered suitable includes, but is not limited to, a length that is greater than the length of catheter 500 and/or main body 502.

Light source 548 is operatively connected or attached to optical fiber proximal end 544 and includes a fiber coupling 550 which provides communication between the light source 548 and optical fiber 542. Light generated by light source 548 travels through the light path defined by optical fiber 542 and is emitted axially from optical fiber distal end 546.

Any suitable light source 548 can be used, and skilled artisans will be able to select a suitable light source according to a particular embodiment based on various considerations, including the desired bodily passage within which a medical device is intended to be used. Example light sources considered suitable include, but are not limited to, commercially-available light sources such as xenon, laser, LED, and halogen light sources.

It is noted that while a single optical fiber 542 is described and illustrated, two or more different optical fibers can be used in combination, or independently, to provide axially-directed and/or radially directed light. The two optical fibers can extend through the same or different lumens of an elongate main body 502 and can be operatively connected or attached to the same or two different light sources.

Additional structure can be attached to the catheters described herein to facilitate the inflation and deflation of the balloon(s). For example, a syringe or other suitable structure can be attached to the inflation port(s) using any suitable connection, such as a luer lock connection. The fluid used to inflate a balloon can be stored within the syringe and/or inflation lumen(s) and can be introduced into and removed from the inflation chamber(s) by operating the syringe using conventional practices.

FIG. 11 illustrates the exemplary catheter 500 and optical fiber 542 illustrated in FIG. 10 disposed through cannula lumen 388 of medical device 310. Elongate member 312 is illustrated in the first straight, or substantially straight, configuration and first balloon 504 and second balloon 506 of catheter 500 are illustrated in an inflated configuration.

In the illustrated embodiment, main body proximal end 508 is disposed proximal to cannula proximal end 384 and main body distal end 510 is disposed distal to elongate member distal end 320. In addition, optical fiber proximal end (not shown) is disposed proximal to main body proximal end 508 and optical fiber distal end 546 is disposed distal to main body distal end 510.

While catheter 500 has been described and illustrated as disposed through cannula lumen 388 and optical fiber 542 has been described and illustrated as disposed through secondary device lumen 518, any suitable device can be passed through any lumen and/or passageway of a medical device (e.g., second lumen 28, second lumen 128, third lumen 166, second lumen 228, third lumen 266, third lumen 366, passageway 378, cannula lumen 388, secondary device lumen 518). Skilled artisans will be able to select a suitable device to pass through a lumen and/or passageway of a medical device according to a particular embodiment based on various considerations, including the desired procedure is intended to be performed. Example devices considered suitable to pass through a lumen and/or passageway defined by a medical device include, but are not limited to, catheters, balloon catheters, suction devices, graspers, cutting tools, illuminating members, optical fibers, cameras, chip-in-tip fiber optics, imaging devices, imaging fibers, and any other device considered suitable for a particular application. Examples of chip-in-tip fiber optics considered suitable include, but are not limited to, an elongate member or fiber optic having a CCD image sensor or a CMOS image sensor disposed within or on the distal end of the elongate member or fiber optic. Thus, a secondary device can be selected from the group of secondary devices described herein or from other suitable groups of secondary devices.

Thus, a secondary device having a secondary device proximal end and a secondary device distal end can be passed through a lumen and/or passageway of a medical device (e.g., medical device 10, medical device 310, catheter 500, medical device 610, medical device 710), or portion thereof, such that the secondary device distal end is disposed proximal to, at, near, or distal to the distal end of the medical device. It is considered advantageous to advance a secondary device distal end to the distal end of a medical device, such as those described herein, at least because this allows for the secondary device to be introduced into a bodily passage, such as a sinus cavity, to provide visualization of the bodily passage and/or treatment to the bodily passage.

For example, an imaging device, such as a scope comprising a chip-in-tip, having a proximal end and a distal end, can be passed through passageway 378 to provide visualization during advancement of medical device 310 through a bodily passage and/or during treatment of the bodily passage. Any suitable imaging device can be used in combination with any of the medical devices described herein, and skilled artisans will be able to select a suitable device according to a particular embodiment based on various considerations, including the desired bodily passage within which a medical device is intended to be used. An example imaging device considered suitable includes, but is not limited to, an eyeMAX (eyeMAX is a registered trademark of Richard Wolf GmbH Corporation of Knittlingen, Federal Republic of Germany) endoscope with chip on-the-tip, or chip-in-tip, technology.

While various devices have been described as being passed through a lumen and/or passageway of a medical device (e.g., second lumen 28, second lumen 128, third lumen 166, second lumen 228, third lumen 266, third lumen 366, passageway 378, cannula lumen 388, secondary device lumen 518), one or more devices can be embedded within the wall of an elongate member of a medical device, or attached to a portion of a medical device (e.g., elongate member). Skilled artisans will be able to select a suitable device to embed within the wall of an elongate member according to a particular embodiment based on various considerations, including the desired procedure intended to be performed. Example number of devices considered suitable to embed within the wall of an elongate member of a medical device include, but are not limited to, one, at least one, two, a plurality, three, four, and any other number considered suitable for a particular application. Example devices considered suitable to embed within the wall of an elongate member of a medical device include, but are not limited to, illuminating members, optical fibers, cameras, chip-in-tip fiber optics, imaging devices, imaging fibers, and any other device considered suitable for a particular application. For example, the wall of an elongate member can include one or more embedded optical fibers and/or one or more imaging devices to provide illumination and/or imaging during advancement of the medical device through a bodily passage and/or during treatment of the bodily passage.

When an imaging device, such as a camera, is disposed through, attached, or embedded within, a portion of a medical device, such as those described herein, the imaging device can be adapted to capture images from the distal end of the medical device and/or from the circumference of the medical device at any point along the medical device length. The imaging device can be adapted to be attached to a display and/or power source and to provide still and/or live footage to the display for review by a user. Alternatively, multiple imaging devices can be used in conjunction with, or separate from, one another. An imaging device can comprise a wired and/or wireless camera or chip that is adapted to transmit images to a display and/or storage device.

FIGS. 12 and 12A illustrate another exemplary medical device 610. Medical device 610 is similar to medical device 10 illustrated in FIGS. 1, 1A, 2, and 3, and described above, except as detailed below. Reference numbers in FIGS. 12 and 12A refer to the same structural element or feature referenced by the same number in FIGS. 1, 1A, 2, and 3, offset by 600. Thus, medical device 610 comprises an elongate member 612, a handle 614, and a wire member 616.

In the illustrated embodiment, handle 614 is disposed along the length of elongate member 612 between elongate member proximal end 618 and elongate member distal end 620 and comprises a handle proximal end 635, a handle distal end 637, a housing 638, and an actuator 640 (e.g., lever 651). Housing 638 has a housing wall 642 that defines a housing cavity 644, a first housing opening 646, a second housing opening 648, and a third housing opening 650. Each of the first housing opening 646, second housing opening 648, and third housing opening 650 extends through the housing wall 642 and provides access to housing cavity 644.

In the illustrated embodiment, actuator 640 comprises lever 651 having a lever first end 652, lever second end 654, and a wall 653 that defines an opening 655, a first aperture 657, and attachment apertures 659. Each of the opening 655, first aperture 657, and attachment apertures 659 extends through the wall 653 of lever 651. Lever first end 652 is disposed within the housing cavity 644 and lever second end 654 is disposed outside of housing cavity 644. Opening 655 is defined on lever 651 between lever first end 652 and lever second end 654 and is adapted to receive a portion of elongate member 612. Thus, elongate member 612 is disposed through opening 655. First aperture 657 is defined on lever 651 between opening 655 and lever first end 652 and is adapted to receive a portion of wire member 616.

Each attachment aperture 659 is adapted to receive a portion of a pin 656 to pivotably attach lever 651 to housing wall 642 such that lever 651 can move within second housing opening 648 between a lever first position and a lever second position. Movement of lever 651 between the lever first position and the lever second position results in movement of elongate member 612 between a first straight, or substantially straight, configuration, and a curved configuration.

While pins 656 have been illustrated and described as providing pivotable attachment between lever 651 and housing 638, any suitable method of attachment between an actuator (e.g., lever) and a housing can be used. Skilled artisans will be able to select a suitable method of attachment between an actuator and a housing according to a particular embodiment based on various considerations, including the materials forming the actuator and the housing. An example method of attachment considered suitable between an actuator and a housing includes, but is not limited to, using a threaded attachment device (e.g., screw), a shaft, and any other method of attachment considered suitable for a particular application.

In the illustrated embodiment, wire member 616 comprises a wire member first end 658 and a wire member second end (not shown). Wire member first end 658 is attached to lever 651 between lever first end 652 and lever second end 654 by passing wire member 616 through first aperture 657 and wrapping wire member 616 around lever 651, as described herein.

While wire member first end 658 has been described and illustrated as being passed through first aperture 657, a wire member can be connected to a lever and/or actuator using any suitable method of attachment, and skilled artisans will be able to select a suitable method of attachment between a wire member and a lever and/or actuator according to a particular embodiment based on various considerations, including the materials forming the wire member and the lever and/or actuator. Example methods of attachment are described herein.

FIGS. 13, 14, and 14A illustrate another exemplary medical device 710. Medical device 710 is similar to medical device 310 illustrated in FIGS. 6, 6A, 7, and 8, and described above, except as detailed below. Reference numbers in FIGS. 13, 14, and 14A refer to the same structural element or feature referenced by the same number in FIGS. 6, 6A, 7, and 8, offset by 400. Thus, medical device 710 comprises an elongate member 712, a handle 714, and a wire member 716.

In the illustrated embodiment, medical device 710 comprises a cannula 770 that is partially disposed through elongate member 712 and handle 714. Handle 714 comprises an actuator 740 and a locking mechanism 776. Actuator 740 comprises a lever 751, a support arm 772, and a connecting member 774. Handle 714 omits the inclusion of a passageway (e.g., passageway 378 illustrated in FIGS. 6, 6A, and 8). Housing 738 is disposed within opening 842 defined by the wall 836 of lever 751, as described below. While handle 714 omits the inclusion of a passageway, any suitable number of passageways can be included in a handle, and skilled artisans will be able to select a suitable number of passageways to include in a handle according to a particular embodiment based on various considerations, including the number of lumens defined by an elongate member. Example number of passageways considered suitable to include in a handle include, but are not limited to, one, at least one, two, a plurality, three, four, and any other number considered suitable for a particular application.

In the illustrated embodiment, handle 714 is disposed on elongate member proximal end 718 such that elongate member proximal end 718 is positioned within housing cavity 744. This is considered advantageous at least because it provides stability of medical device 710 during use and limits the devices and/or structures positioned proximal to handle 714. Cannula 770 is slidingly disposed through a portion of housing 738 and a portion of elongate member 712. Cannula 770 is slidingly disposed through housing first opening 746 such that the cannula proximal end 784 is disposed proximal to housing 738 and outside of housing cavity 744.

In the illustrated embodiment, lever 751 has a lever first end 752, a lever second end 754, a first lever arm 830, a second lever arm 832, a third lever arm 834 and a lever wall 836 that defines attachment apertures 838, first aperture 840, opening 842, and lever protuberance 844. Each of the first lever arm 830 and second lever arm 832 extends from the lever first end 752 to the lever second end 754 and is pivotably attached to housing wall 742 by pins 756. Third lever arm 834 extends between first lever arm 830, second lever arm 832, and into housing second opening 748 and is adapted to be attached to wire member 716. Each attachment aperture 838 is disposed between the lever first end 752 and lever second end 754 and first aperture 840 is disposed between lever second end 754 and attachment apertures 838. A first pin 756 is disposed through a first attachment aperture 838 and a second pin 756 is disposed through a second attachment aperture 838. Lever protuberance 844 extends radially inward into opening 842 and is disposed between first lever arm 830 and second lever arm 832 on lever first end 752. Alternatively, lever protuberance 844 can extend from first lever arm 830 to second lever arm 832. Housing 738 is disposed within opening 842 and lever 751 is adapted to move with respect to housing 738 between a lever first position and a lever second position, as described in more detail herein.

Support arm 772 has a support arm first end 796 and a support arm second end 798. Support arm first end 796 is pivotably attached to lever second end 754 by pin 797 that extends through an aperture defined by the wall of support arm 772 and support arm second end 798 is pivotably attached to connecting member 774 by pin 799 that extends through an aperture defined by the wall of support arm. Alternatively, support arm second end 798 can be pivotably attached to cannula 770. Connecting member 774 has a connecting member proximal end 800, a connecting member distal end 802, and defines a connecting member lumen 804 that extends from a first connecting member opening on connecting member proximal end 800 to a second connecting member opening on connecting member distal end 802. Connecting member 774 is attached to cannula 770 between the cannula proximal end 784 and cannula distal end 786.

In the illustrated embodiment, first lever arm 830, second lever arm 832, support arm 772, and connecting member 774 are disposed outside of housing 738 (e.g., not in housing cavity 744). This configuration is considered advantageous at least because it reduces the structural features within housing cavity 744.

Locking mechanism 776 is formed from a portion of housing 738 and comprises a locking mechanism first end 810, a locking mechanism second end 812, a locking mechanism exterior surface 814, a locking mechanism interior surface 816, and defines a locking mechanism first protuberance 818 and a plurality of locking mechanism second protuberances 820. Locking mechanism first end 810 is free of housing 738 and locking mechanism second end 812 is pivotably attached to housing 738. Locking mechanism first protuberance 818 is defined on the exterior surface 814 of locking mechanism 776 and extends outward and away from housing cavity 744. Each protuberance of the plurality of locking mechanism second protuberances 820 is defined on the exterior surface 814 of locking mechanism 776 and extends outward and away from the housing cavity 744. In the illustrated embodiment, the plurality of locking mechanism second protuberances 820 is complementary to protuberance 844 defined by lever 751.

Locking mechanism 776 has a locking mechanism first position and a locking mechanism second position. In the locking mechanism first position, locking mechanism 776 is engaged with, or interacts with, lever protuberance 844 such that movement of lever 751 is prevented, or substantially prevented. As lever 751 is moved along the wall 742 of housing 738 its position is maintained by locking mechanism 776. Thus, the housing 738 and lever 751 are structurally arranged such that locking mechanism 776 and lever 751 are engaged, or interacting, with one another without the application of outside forces. In the locking mechanism second position, locking mechanism 776 is free of lever 751 such that lever 751 can be moved between its lever first position and lever second position. Locking mechanism 776 can be moved from the locking mechanism first position to the locking mechanism second position by applying a radially inward force on locking mechanism protuberance 818 such that locking mechanism first end 810 moves inward into, or towards, housing cavity 744. This results in disengagement of the plurality of locking mechanism second protuberances 820 and lever protuberance 844. This is considered advantageous at least because it provides a mechanism for maintaining the position of lever 751 when elongate member 712 has defined a desired radius of curvature. Thus, lever 751 is adapted to be releasably fixed in the lever second position until additional forced is placed on lever 751 to move it along the wall 742 of housing 738 or additional force is placed on locking mechanism 776 to free lever 751 of locking mechanism 776.

The inclusion of a locking mechanism 776 is considered advantageous at least because it provides a mechanism to prevent, or substantially prevent, movement of wire member 716, lever 751, connecting member 774, and cannula 770, when a desired radius of curvature has been defined by elongate member 712. For example, it is considered advantageous to include a locking mechanism 776 at least because it allows the configuration of elongate member 712 to be fixed, or substantially fixed, when treatment is being performed (e.g., dilation of a bodily passage).

In use, movement of lever first end 752 away from cannula proximal end 784, as shown by arrow 762, from the lever first position to the lever second position causes wire member 716 and support arm second end 798 to move in a proximal, or substantially proximal, direction. This results in cannula 770 being moved in the proximal direction, tension in wire member 716, and movement of elongate member 712 from a straight, or substantially straight, configuration, to a curved configuration in which elongate member 712 defines a curve. Movement of lever first end 752 towards cannula proximal end 784, in a direction opposite, or substantially opposite, that of arrow 762, advances cannula 770 towards elongate member distal end, reduces, or eliminates, tension in wire member 716, and results in elongate member 712 returning to its straight, or substantially straight, configuration.

Various methods of treatment are described herein. While the methods described herein are shown and described as a series of acts, it is to be understood and appreciated that the methods are not limited by the order of acts, as some acts may in accordance with these methods, occur in different orders, and/or concurrently with other acts described herein.

Figure 18:
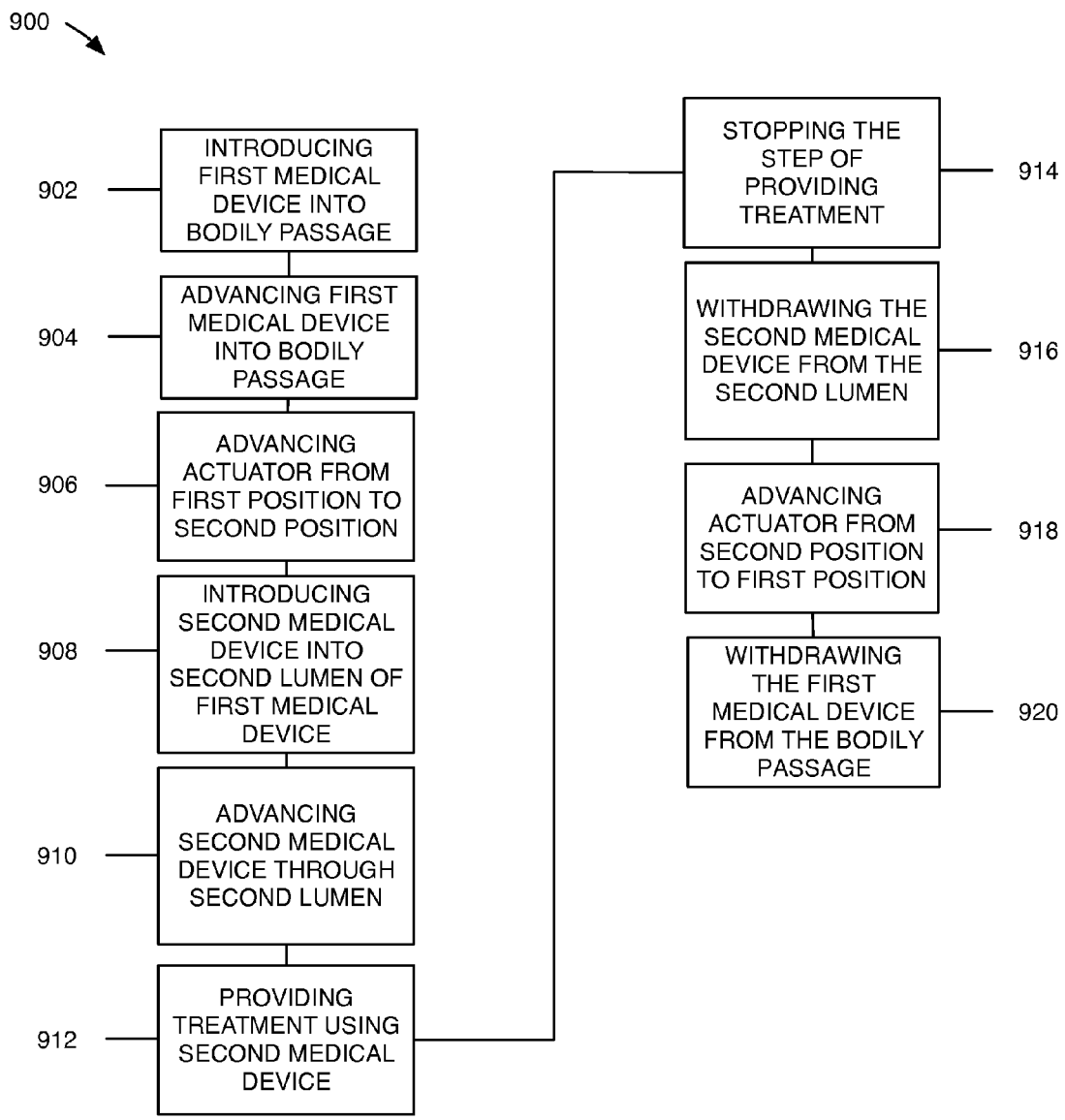
FIG. 18 is a flowchart representation of a method of treatment.

FIG. 18 is a flowchart representation of a method 900 of treating tissue in a bodily passage defined by a bodily passage wall.

A step 902 comprises introducing a first medical device having a first proximal end and a first distal end into the bodily passage such that the first distal end is disposed within the bodily passage. The first medical device comprises an elongate member, a handle, and a wire member. The elongate member has an elongate member proximal end, an elongate member distal end, and defines a first lumen and a second lumen. The handle is disposed on the elongate member and has an actuator moveable between an actuator first position and an actuator second position. The actuator comprises a first portion and a second portion. The wire member is partially disposed within the first lumen and has a wire member first end attached to the first portion of the actuator and a wire member second end attached to the elongate member. The elongate member is moveable between a substantially straight configuration when the actuator is in the actuator first position and a curved configuration when the actuator is in the actuator second position. Another step 904 comprises advancing the first medical device into the bodily passage such that the first distal end is disposed adjacent a point of treatment. Another step 906 comprises advancing the actuator of the first medical device from the actuator first position to the actuator second position such that the elongate member moves from the substantially straight configuration to the curved configuration. Another step 908 comprises introducing a second medical device having a second proximal end and a second distal end into the second lumen defined by the first medical device such that the second distal end is disposed with the second lumen. Another step 910 comprises advancing the second medical device through the second lumen defined by the first medical device such that the second distal end is disposed distal to the first distal end. Another step 912 comprises providing treatment using the second medical device. Another step 914 comprises stopping the step of providing treatment using the second medical device. Another step 916 comprises withdrawing the second medical device from the second lumen defined by the first medical device such that the second distal end is disposed proximal to the first proximal end. Another step 918 comprises advancing the actuator of the first medical device from the actuator second position to the actuator first position. Another step 920 comprises withdrawing the first medical device from the bodily passage such that the first distal end is disposed outside of the bodily passage.

Step 902 can be accomplished using any suitable medical device according to an embodiment, such as the embodiments described and illustrated herein. Skilled artisans will be able to select a suitable medical device to introduce into a bodily passage according to a particular embodiment based on various considerations, including the treatment intended to be performed. Examples of medical devices considered suitable to introduce into a bodily passage to complete one or more steps and/or methods described herein include, but are not limited to, medical device 10, medical device 310, medical device 610, medial device 710, medical devices that include an elongate member according to an embodiment (e.g., elongate member 112, elongate member 212), medical devices that include a cannula according to an embodiment (e.g., cannula 370'), and any other medical device considered suitable for a particular application.

Step 902 can be accomplished by applying a distally-directed force on any suitable portion of the first medical device (e.g., handle) such that the first distal end is disposed within the bodily passage. Step 902 can be accomplished by introducing the first medical device into any suitable bodily passage. Skilled artisans will be able to select a suitable bodily passage to introduce a medical device according to a particular embodiment based on various considerations, including the treatment intended to be performed. Example bodily passages considered suitable to introduce a medical device include, but are not limited to, a sinus passage, a sinus cavity, and any other bodily passage considered suitable for a particular application.

Step 904 can be accomplished by applying a distally-directed force on any suitable portion of the first medical device (e.g., handle) such that the first distal end is advanced into the bodily passage and is disposed adjacent a point of treatment. Alternatively, the first distal end of a medical device can be advanced into a bodily passage such that it is disposed at, near, proximal to, distal to, or at any other suitable position relative to a point of treatment.

Step 906 can be accomplished by applying either a proximally-directed force or a distally-directed force on an actuator such that it is advanced from the actuator first position to the actuator second position and the elongate member moves from the substantially straight configuration to the curved configuration. The directionality of the force will depend on the structural arrangement of the handle and actuator of the first medical device. For example, with respect to medical device 10, a proximally-directed force can be applied the actuator to advance the actuator from the actuator first position to the actuator second position. Alternatively, with respect to medical device 310, a distally-directed force can be applied to the actuator to advance the actuator from the actuator first position to the actuator second position.

Alternative to completing step 906, a step that comprises advancing the actuator from the actuator first position to a position between the actuator first position and the actuator second position can be completed such that the elongate member moves from the substantially straight configuration to the curved configuration. For example, this step can be completed to achieve a radius of curvature that is greater than the radius of curvature when the actuator is in the actuator second position.

An optional step comprises applying torque to any suitable portion of the first medical device (e.g., handle) such that the first medical device is rotated and the first distal end is directed towards the point of treatment, or an opening defined by the bodily passage wall.

Another optional step comprises advancing the first distal end of the first medical device towards the bodily passage wall, or an opening defined by the bodily passage wall (e.g., sinus passage, sinus cavity, ostium). This step can be accomplished by applying a force on any suitable portion of the first medical device (e.g., handle) in a direction such that the first distal end is advanced towards the bodily passage wall, or an opening defined by the bodily passage wall (e.g., in a direction that extends on an axis that passes through the longitudinal axis of the first medical device).

Another optional step comprises introducing the first distal end of the first medical device into an opening defined by the bodily passage wall. This step can be accomplished by applying a force on any suitable portion of the first medical device (e.g., handle) in a direction such that the first distal end is introduced into the opening defined by the bodily passage (e.g., in a direction that extends on an axis that passes through the longitudinal axis of the first medical device). Optionally, the first distal end can be advanced through the opening defined by the bodily passage wall and into another bodily passage (e.g., sinus passage, sinus cavity).

Another optional step comprises maintaining the position of the actuator when the actuator is in the actuator second position, or in a position between the actuator first position and the actuator second position. In embodiments that include a locking mechanism, this step can be accomplished by activating the locking mechanism (e.g., by applying a radially inward force on a portion of a locking mechanism) to maintain the radius of curvature defined by the elongate member when the actuator is in the actuator second position, or in a position between the actuator first position and the actuator second position. Alternatively, this step can be accomplished by applying a force on the actuator (e.g., radially inward force, proximally-directed force, distally-directed) such that the radius of curvature defined by the elongate member is maintained when the actuator is in the actuator second position, or in a position between the actuator first position and the actuator second position.

Step 908 can be accomplished using any suitable medical device, such as the embodiments described and illustrated herein. Skilled artisans will be able to select a suitable second medical device to introduce into a first medical device according to a particular embodiment based on various considerations, including the treatment intended to be performed. Examples of medical devices considered suitable to introduce into a first medical device to complete one or more steps and/or methods described herein include, but are not limited to, catheters, catheter 500, balloon catheters, suction devices, graspers, cutting tools, illuminating members, optical fibers, cameras, scopes, chip-in-tip fiber optics, imaging devices, imaging fibers, and any other medical device considered suitable for a particular application. Alternative to passing a second medical device through a first medical device, a second medical device can be preloaded within a lumen defined by an elongate member of a first medical device such that step 908 can be omitted.

Step 908 can be accomplished by applying a distally-directed force on any suitable portion of the second medical device such that the second distal end of the second medical device is disposed within the second lumen defined by the elongate member of the first medical device.

Step 910 can be accomplished by applying a distally-directed force on any suitable portion of the second medical device such that the second medical device is advanced through the second lumen and the second distal end is disposed distal to the first distal end. For example, this step can be accomplished such that the second distal end is disposed at, near, adjacent, proximal to, or distal to a point of treatment.

An optional step comprises advancing the second distal end towards the bodily passage wall, or an opening defined by the bodily passage wall (e.g., sinus passage, ostium). This step can be accomplished by applying a distally-directed force on any suitable portion of the second medical device such that the second distal end is advanced towards the bodily passage wall, or the opening defined by the bodily passage wall. This optional step can be completed subsequent to step 906 such that the second distal end is directed towards a desired point of treatment as it is advanced.

Another optional step comprises introducing the second distal end of the second medical device into an opening defined by the bodily passage wall. This step can be accomplished by applying a distally-directed force on any suitable portion of the second medical device in a direction such that the second distal end is introduced into the opening defined by the bodily passage. Optionally, the second distal end can be advanced through the opening defined by the bodily passage wall and into another bodily passage (e.g., sinus passage, sinus cavity).

For example, the second medical device can comprise an imaging device, such as a scope, and can include chip-in-tip fiber optic, a proximal end and a distal end. The imaging device can be passed through the second lumen of the first medical device and/or advanced through an opening defined by the bodily passage wall (e.g., ostium) and into a second bodily passage (e.g., sinus cavity) to provide visualization during advancement of the first and/or second medical device through a bodily passage and/or during treatment. Any suitable imaging device can be used in combination with any of the medical devices described herein, and skilled artisans will be able to select a suitable imaging device according to a particular embodiment based on various considerations, including the desired bodily passage within which a medical device is intended to be used. Optional steps include activating the imaging device and deactivating the imaging device.

Step 912 can be accomplished using conventional techniques and will depend on the medical device that has been advanced through the second lumen of the first medical device. For example, if a catheter, such as catheter 500, has been passed through the second lumen, the step of providing treatment can include a step that comprises activating the light source such that light is emitted axially from the optical fiber, and/or a step of introducing a fluid into the first balloon such that the first balloon is moved from the deflated configuration to the inflated configuration, and/or a step of introducing a fluid into the second balloon such that the second balloon is moved from the deflated configuration to the inflated configuration.

Step 914 can be accomplished using convention techniques and will depend on the medical device that has been advanced through the second lumen of the first medical device. For example, if a catheter, such as catheter 500, has been passed through the second lumen, the step of stopping the step of providing treatment can include a step that comprises deactivating the light source such that light is not emitted axially from the optical fiber, and/or a step of removing a portion, or the entirety, of the fluid disposed within the first balloon to move the first balloon from the inflated configuration to the deflated configuration, and/or a step of removing a portion, or the entirety, of the fluid disposed within the second balloon to move the second balloon from the inflated configuration to the deflated configuration.

In embodiments in which the elongate member of the first medial device defines more than two lumens (e.g., a third lumen), an optional step comprises introducing a third medical device having a third proximal end and a third distal end into the third lumen such that the third distal end is disposed within the third lumen. Another optional step comprises advancing third medical device through the third lumen such that the third distal end is disposed distal to the first distal end. Another optional step comprises providing treatment using the third medical device. Another optional step comprises stopping the step of providing treatment using the third medical device. Another optional step comprises withdrawing the third medical device from the third lumen such that the third distal end is disposed proximal to the first proximal end. Examples of suitable medical devices considered suitable to complete these optional step are described above with respect to step 908 and herein. In addition, examples of completing one or more of these optional steps are described herein with respect to the second medical device.

Step 916 can be accomplished by applying a proximally-directed force on any suitable portion of the second medical device until it has been withdrawn from the first medical device and such that the second distal end is disposed proximal to the first proximal end. Optionally, step 916 can be omitted from method 900.

Step 918 can be accomplished by applying either a proximally-directed force or a distally-directed force on an actuator such that it is advanced from the actuator second position to the actuator first position and the elongate member moves from the curved configuration to the substantially straight configuration. The directionality of the force will depend on the structural arrangement of the handle and actuator of the first medical device. For example, with respect to medical device 10, a distally-directed force can be applied the actuator to advance the actuator from the actuator second position to the actuator first position. Alternatively, with respect to medical device 310, a proximally-directed force can be applied to the actuator to advance the actuator from the actuator first position to the actuator second position. Optionally, step 918 can be omitted from method 900.

Step 920 can be accomplished by applying a proximally-directed force on any suitable portion of the first medical device (e.g., handle) until it has been withdrawn from the bodily passage and such that the first distal end of the first medical device is disposed proximal to and outside of the bodily passage.

While step 916, step 918, and step 920 have been described as separate steps, step 916, step 918, and/or step 920 can be completed in combination with one another.

While various steps, alternative steps, and optional steps have been described above with respect to method 900, these steps, alternative steps, and optional steps can be included in, accomplished concurrently with, and/or accomplished in the alternative to, the methods, steps, alternative steps, and/or optional steps described below with respect method 1000.

Figure 19:
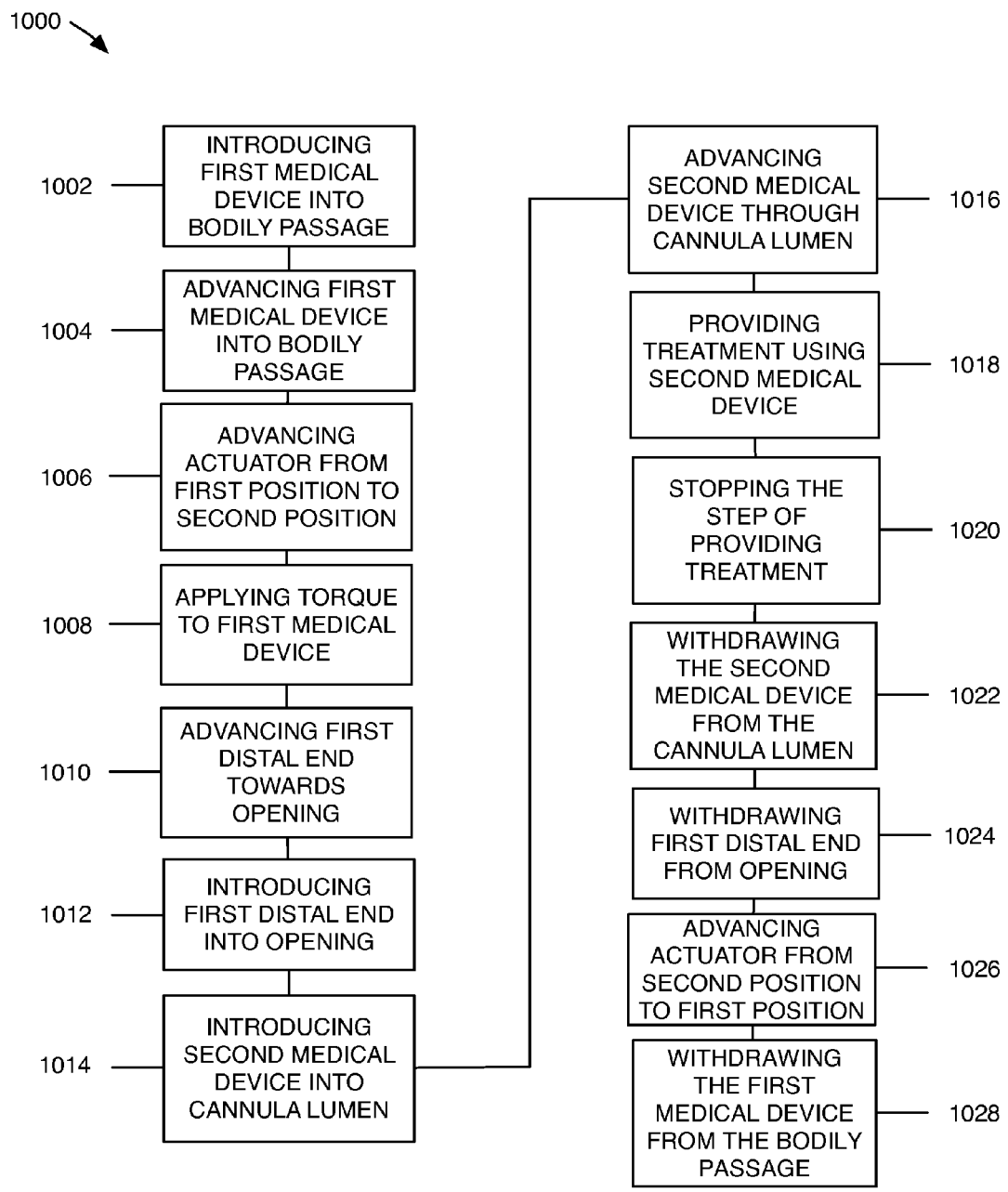
FIG. 19 is a flowchart representation of another method of treatment.

FIG. 19 is a flowchart representation of a method 1000 of treating tissue in a bodily passage wall. The bodily passage wall defines a bodily passage and an opening.

A step 1002 comprises introducing a first medical device having a first proximal end and a first distal end into the bodily passage such that the first distal end is disposed within the bodily passage. The first medical device comprises an elongate member, a handle, a wire member, and a cannula. The elongate member has an elongate member proximal end, an elongate member distal end, and defines a first lumen and a second lumen. The handle is disposed on the elongate member and has an actuator moveable between an actuator first position and an actuator second position. The actuator comprises a first portion and a second portion. The wire member has a wire member first end attached to the first portion of the actuator and a wire member second end attached to the elongate member. The cannula has a cannula proximal end attached to the second portion of the actuator and a cannula distal end disposed within the second lumen and defines a cannula lumen. The cannula is moveable between a cannula first position when the actuator is in the actuator first position and a cannula second position when the actuator is in the actuator second position. In the cannula first position the cannula distal end is disposed at a first location within the second lumen. In the cannula second position the cannula distal end is disposed at a second location in the second lumen that is proximal to the first location. The elongate member is moveable between a substantially straight configuration when the actuator is in the actuator first position and a curved configuration when the actuator is in the actuator second position. Another step 1004 comprises advancing the first medical device into the bodily passage such that the first distal end is disposed adjacent a point of treatment. Another step 1006 comprises advancing the actuator of the first medical device from the actuator first position to the actuator second position such that the cannula moves from the cannula first position to the cannula second position and the elongate member moves from the substantially straight configuration to the curved configuration. Another step 1008 comprises applying torque to the first medical device such that the first distal end is directed towards the opening defined by the bodily passage wall. Another step 1010 comprises advancing the first distal end towards the opening defined by the bodily passage wall. Another step 1012 comprises introducing the first distal end of the first medical device into the opening defined by the bodily passage wall. Another step 1014 comprises introducing a second medical device having a second proximal end and a second distal end into the cannula lumen such that the second distal end is disposed with the cannula lumen. Another step 1016 comprises advancing the second medical device through the cannula lumen such that the second distal end is disposed distal to the first distal end. Another step 1018 comprises providing treatment using the second medical device. Another step 1020 comprises stopping the step of providing treatment using the second medical device. Another step 1022 comprises withdrawing the second medical device from the cannula lumen such that the second distal end is disposed proximal to the first proximal end. Another step 1024 comprises withdrawing the first distal end from the opening defined by the bodily passage wall. Another step 1026 comprises advancing the actuator of the first medical device from the actuator second position to the actuator first position. Another step 1028 comprises withdrawing the first medical device from the bodily passage such that the first distal end is disposed outside of the bodily passage.

Step 1002 can be accomplished using any suitable medical device according to an embodiment, such as the embodiments described and illustrated herein. Skilled artisans will be able to select a suitable medical device to introduce into a bodily passage according to a particular embodiment based on various considerations, including the treatment intended to be performed. Examples of medical devices considered suitable to introduce into a bodily passage to complete one or more steps and/or methods described herein include, but are not limited medical device 310, medial device 710, medical devices that include an elongate member according to an embodiment (e.g., elongate member 112, elongate member 212), medical devices that include a cannula according to an embodiment (e.g., cannula 370'), and any other medical device considered suitable for a particular application.

Step 1002 can be accomplished as described above with respect to step 902 and by introducing the first medical device into any suitable bodily passage. Skilled artisans will be able to select a suitable bodily passage to introduce a medical device according to a particular embodiment based on various considerations, including the treatment intended to be performed. Example bodily passages considered suitable to introduce a medical device include, but are not limited to, a sinus passage, a sinus cavity, and any other bodily passage considered suitable for a particular application.

Step 1004 can be accomplished as described above with respect to step 904 and the alternatives described relative to step 904. For example, step 1004 can be accomplished such that first distal end is disposed adjacent the opening defined by said bodily passage wall.

Step 1006 can be accomplished as described above with respect to step 906 and the alternatives described relative to step 906 and such that the cannula moves from the first position to the second position and the elongate member moves from the substantially straight configuration to the curved configuration. For example, with respect to medical device 310, a distally-directed force can be applied the actuator to advance the actuator from the actuator first position to the actuator second position. Alternatively, with respect to medical device 710, a proximally-directed force can be applied to the actuator to advance the actuator from the actuator first position to the actuator second position.

Step 1008 can be accomplished by applying torque to any suitable portion of the first medical device (e.g., handle) such that the first medical device is rotated and the first distal end is directed towards the opening (e.g., ostium) defined by the bodily passage wall.

Step 1010 can be accomplished by applying a force on any suitable portion of the first medical device (e.g., handle) in a direction such that the first distal end is advanced towards the opening defined by the bodily passage wall (e.g., in a direction that extends on an axis that passes through the longitudinal axis of the first medical device) and the first distal end is disposed within, or beyond, the opening defined by the bodily passage wall.

Step 1012 can be accomplished by applying a force on any suitable portion of the first medical device (e.g., handle) in a direction such that the first distal end is introduced into the opening defined by the bodily passage (e.g., in a direction that extends on an axis that passes through the longitudinal axis of the first medical device). Optionally, the first distal end can be advanced through the opening defined by the bodily passage wall and into another bodily passage (e.g., sinus passage, sinus cavity).

An optional step comprises maintaining the position of the actuator when the actuator is in the actuator second position, or in a position between the actuator first position and the actuator second position. In embodiments that include a locking mechanism, this step can be accomplished by activating the locking mechanism (e.g., by applying a radially inward force on a portion of a locking mechanism) to maintain the position of the cannula and the radius of curvature defined by the elongate member when the actuator is in the actuator second position, or in a position between the actuator first position and the actuator second position. Alternatively, this step can be accomplished by applying a force on the actuator (e.g., radially inward force, proximally-directed force, distally-directed) such that the position of the cannula and the radius of curvature defined by the elongate member is maintained when the actuator is in the actuator second position, or in a position between the actuator first position and the actuator second position.

Step 1014 can be accomplished using any suitable medical device, such as the embodiments described and illustrated herein. Skilled artisans will be able to select a suitable second medical device to introduce into a first medical device according to a particular embodiment based on various considerations, including the treatment intended to be performed. Examples of medical devices considered suitable to introduce into a first medical device are described above with respect to method 900 and herein. Alternative to passing a second medical device through a first medical device, a second medical device can be preloaded within a lumen defined by an elongate member of a first medical device such that step 1014 can be omitted.

Step 1014 can be accomplished by applying a distally-directed force on any suitable portion of the second medical device such that the second distal end of the second medical device is disposed within the cannula lumen.

Step 1016 can be accomplished by applying a distally-directed force on any suitable portion of the second medical device such that the second medical device is advanced through the cannula lumen and the second distal end is disposed distal to the first distal end. This step can be accomplished such that the second distal end is disposed at, near, adjacent, proximal to, or distal to a point of treatment.

An optional step comprises advancing the second distal end towards the opening defined by the bodily passage wall (e.g., sinus passage, ostium). This step can be accomplished by applying a distally-directed force on any suitable portion of the second medical device such that the second distal end is advanced towards the opening defined by the bodily passage wall.

Another optional step comprises introducing the second distal end of the second medical device into the opening defined by the bodily passage wall. This step can be accomplished by applying a distally-directed force on any suitable portion of the second medical device in a direction such that the second distal end is introduced into the opening defined by the bodily passage. Optionally, the second distal end can be advanced through the opening defined by the bodily passage wall and into another bodily passage (e.g., sinus passage, sinus cavity).

For example, the second medical device can comprises an imaging device, such as a scope, and can include chip-in-tip fiber optic, a proximal end and a distal end. The imaging device can be passed through the cannula lumen of the first medical device and/or advanced through the opening defined by the bodily passage wall (e.g., ostium) and into a second bodily passage (e.g., sinus cavity) to provide visualization during advancement of the first and/or second medical device through a bodily passage and/or during treatment. Any suitable imaging device can be used in combination with any of the medical devices described herein, and skilled artisans will be able to select a suitable imaging device according to a particular embodiment based on various considerations, including the desired bodily passage within which a medical device is intended to be used. When an imaging device has been advanced through the cannula lumen, the optional steps described above can be accomplished such that the second distal end of the imaging device is disposed past the opening defined by the bodily passage wall (e.g., ostium) and into a second bodily passage (e.g., sinus cavity). Optional steps include activating the imaging device and deactivating the imaging device.

Step 1018 can be accomplished using conventional techniques and will depend on the medical device that has been advanced through the cannula lumen. For example, step 1018 can be accomplished as described above with respect to step 912.

Step 1020 can be accomplished using conventional techniques and will depend on the medical device that has been advanced through the cannula lumen. For example, step 1020 can be accomplished as described above with respect to step 914.

Step 1022 can be accomplished as described above with respect to step 916. Optionally, step 1022 can be omitted from method 1000.

Step 1024 can be accomplished by applying a force on any suitable portion of the first medical device (e.g., handle) in a direction such that the first distal end is withdrawn from the opening defined by the bodily passage wall (e.g., in a direction that extends on an axis that passes through the longitudinal axis of the first medical device).

Step 1026 can be accomplished as described above with respect to step 918 and the alternatives described relative to step 918 and such that the cannula moves from the second position to the first position and the elongate member moves from the curved configuration to the substantially straight configuration. For example, with respect to medical device 310, a proximally-directed force can be applied the actuator to advance the actuator from the actuator second position to the actuator first position. Alternatively, with respect to medical device 710, a distally-directed force can be applied to the actuator to advance the actuator from the actuator first position to the actuator second position. Optionally, step 1026 can be omitted from method 1000.

Step 1028 can be accomplished as described above with respect to step 920.

While step 1022, step 1024, step 1026, and step 1028 have been described as separate steps, step 1022, step 1024, step 1026, and/or step 1028 can be completed in combination with one another.

While various steps, alternative steps, and optional steps have been described above with respect to method 1000, these steps, alternative steps, and optional steps can be included in, accomplished concurrently with, and/or accomplished in the alternative to, the methods, steps, alternative steps, and/or optional steps described above with respect method 900.

The foregoing detailed description provides exemplary embodiments of the invention and includes the best mode for practicing the invention. The description and illustration of embodiments is intended only to provide examples of the invention, and not to limit the scope of the invention, or its protection, in any manner.

What is claimed is:

1. A medical device comprising:
an elongate member having an elongate member proximal end, an elongate member distal end, and defining a first lumen and a second lumen;
a handle disposed on the elongate member and having an actuator moveable between an actuator first position and an actuator second position, the actuator having a first portion and a second portion;
a wire member having a wire member first end attached to the first portion of the actuator and a wire member second end disposed within the first lumen and attached to the elongate member; and
a cannula having a cannula proximal end attached to the second portion of the actuator and a cannula distal end disposed within the second lumen, the cannula moveable between a cannula first position when the actuator is in the actuator first position and a cannula second position when the actuator is in the actuator second position, in the cannula first position the cannula distal end is disposed at a first location, in the cannula second position the cannula distal end is disposed at a second location that is proximal to the first location;
wherein the elongate member is moveable between a substantially straight configuration when the actuator is in the actuator first position and a curved configuration when the actuator is in the actuator second position.

2. The medical device of claim 1, wherein the elongate member has an elongate member first portion and an elongate member second portion, the elongate member first portion extending from the elongate member proximal end towards the elongate member distal end to a location between the elongate member proximal end and the elongate member distal end, the elongate member second portion extending from the elongate member distal end towards the elongate member proximal end to a location between the elongate member proximal end and the elongate member distal end;
wherein the elongate member first portion is formed of a first material and the elongate member second portion is formed of a second material; and
wherein the second material is different than the first material.

3. The medical device of claim 1, wherein the elongate member has an elongate member first portion and an elongate member second portion, the elongate member first portion extending from the elongate member proximal end towards the elongate member distal end to a location between the elongate member proximal end and the elongate member distal end, the elongate member second portion extending from the elongate member distal end towards the elongate member proximal end to a location between the elongate member proximal end and the elongate member distal end;
wherein the elongate member first portion is formed of a first material and the elongate member second portion is formed of a second material; and
wherein the second material is flexible relative to the first material.

4. The medical device of claim 1, wherein a portion of the elongate member comprises a coil member.

5. The medical device of claim 1, wherein the handle comprises a locking mechanism that is adapted to releasably fix the actuator in the actuator second position.

6. The medical device of claim 1, wherein the cannula distal end comprises an atraumatic tip.

7. The medical device of claim 1, wherein the elongate member defines a third lumen extending from a third lumen first opening on the elongate member proximal end to a third lumen second opening on the elongate member distal end; and
wherein the cannula defines a fourth lumen extending from a cannula first opening on the cannula proximal end to a cannula second opening on the cannula distal end.

8. The medical device of claim 7, wherein the medical device further comprises a secondary device having a secondary device proximal end and a secondary device distal end;
wherein a portion of the secondary device is disposed in the third lumen; and
wherein the secondary device is selected from the group consisting of a suction device, grasper, cutting tool, illuminating member, optical fiber, camera, chip-in-tip fiber optic, imaging device, and imaging fiber.

9. The medical device of claim 7, wherein the medical device further comprises a balloon catheter having a main body, the main body having a main body proximal end and a main body distal end; and
wherein a portion of the balloon catheter is disposed within the fourth lumen.

10. The medical device of claim 1, wherein the cannula is formed of a substantially rigid material.

11. A medical device comprising:
an elongate member having an elongate member proximal end, an elongate member distal end, and defining a first lumen and a second lumen;
a handle disposed on the elongate member and having an actuator moveable between an actuator first position and an actuator second position, the actuator having a first portion and a second portion;
a wire member having a wire member first end attached to the first portion of the actuator and a wire member second end disposed within the first lumen and attached to the elongate member; and
a cannula having a cannula proximal end attached to the second portion of the actuator and a cannula distal end disposed within the second lumen, the cannula moveable between a cannula first position when the actuator is in the actuator first position and a cannula second position when the actuator is in the actuator second position, in the cannula first position the cannula distal end is disposed at a first location, in the cannula second position the cannula distal end is disposed at a second location that is proximal to the first location;
wherein the elongate member is moveable between a substantially straight configuration when the actuator is in the actuator first position and a curved configuration when the actuator is in the actuator second position; and
wherein the cannula is formed of a substantially rigid material.

12. The medical device of claim 11, wherein the elongate member has an elongate member first portion and an elongate member second portion, the elongate member first portion extending from the elongate member proximal end towards the elongate member distal end to a location between the elongate member proximal end and the elongate member distal end, the elongate member second portion extending from the elongate member distal end towards the elongate member proximal end to a location between the elongate member proximal end and the elongate member distal end;
wherein the elongate member first portion is formed of a first material and the elongate member second portion is formed of a second material; and wherein the second material is different than the first material.

13. The medical device of claim 11, wherein the elongate member has an elongate member first portion and an elongate member second portion, the elongate member first portion extending from the elongate member proximal end towards the elongate member distal end to a location between the elongate member proximal end and the elongate member distal end, the elongate member second portion extending from the elongate member distal end towards the elongate member proximal end to a location between the elongate member proximal end and the elongate member distal end;
   wherein the elongate member first portion is formed of a first material and the elongate member second portion is formed of a second material; and
   wherein the second material is flexible relative to the first material.

14. The medical device of claim 11, wherein a portion of the elongate member comprises a coil member.

15. The medical device of claim 11, wherein the handle comprises a locking mechanism that is adapted to releasably fix the actuator in the actuator second position.

16. The medical device of claim 11, wherein the cannula distal end comprises an atraumatic tip.

17. The medical device of claim 11, wherein the elongate member defines a third lumen extending from a third lumen first opening on the elongate member proximal end to a third lumen second opening on the elongate member distal end; and
   wherein the cannula defines a fourth lumen extending from a cannula first opening on the cannula proximal end to a cannula second opening on the cannula distal end.

18. The medical device of claim 17, wherein the medical device further comprises a secondary device having a secondary device proximal end and a secondary device distal end;
   wherein a portion of the secondary device is disposed in the third lumen; and
   wherein the secondary device is selected from the group consisting of a suction device, grasper, cutting tool, illuminating member, optical fiber, camera, chip-in-tip fiber optic, imaging device, and imaging fiber.

19. The medical device of claim 17, wherein the medical device further comprises a balloon catheter having a main body, the main body having a main body proximal end and a main body distal end; and
   wherein a portion of the balloon catheter is disposed within the fourth lumen.

20. A method of treating tissue in a bodily passage wall defining a bodily passage, the method comprising the steps of:
   introducing a first medical device having a first proximal end and a first distal end into said bodily passage such that the first distal end is disposed within the bodily passage, the first medical device comprising:
      an elongate member having an elongate member proximal end, an elongate member distal end, and defining a first lumen and a second lumen, the elongate member movable between a substantially straight configuration and a curved configuration;
      a handle disposed on the elongate member and having an actuator moveable between an actuator first position and an actuator second position, the actuator having a first portion and a second portion, in the actuator first position the elongate member is in the substantially straight configuration, in the actuator second position the elongate member is in the curved configuration;
      a wire member having a wire member first end attached to the first portion of the actuator and a wire member second end attached to the elongate member; and
      a cannula having a cannula proximal end attached to the second portion of the actuator, a cannula distal end disposed within the second lumen, and defining a cannula lumen, the cannula moveable between a cannula first position when the actuator is in the actuator first position and a cannula second position when the actuator is in the actuator second position, in the cannula first position the cannula distal end is disposed at a first location within the second lumen, in the cannula second position the cannula distal end is disposed at a second location within the second lumen that is proximal to the first location;
   advancing the first medical device into said bodily passage;
   advancing the actuator from the actuator first position to the actuator second position such that the cannula moves from the cannula first position to the cannula second position and the elongate member moves from the substantially straight configuration to the curved configuration;
   introducing a second medical device having a second proximal end and a second distal end into the cannula lumen such that the second distal end is disposed with the cannula lumen;
   advancing the second medical device through the cannula lumen such that the second distal end is disposed distal to the first distal end;
   providing treatment using the second medical device;
   stopping the step of providing treatment using the second medical device;
   withdrawing the second medical device from the cannula lumen such that the second distal end is disposed proximal to the first proximal end;
   withdrawing the first distal end from the opening defined by the bodily passage wall; and
   withdrawing the first medical device from the bodily passage such that the first distal end is disposed outside of the bodily passage.

* * * * *